United States Patent
Wexler et al.

(12) 
(10) Patent No.: US 10,592,763 B2
(45) Date of Patent: *Mar. 17, 2020

(54) APPARATUS AND METHOD FOR USING BACKGROUND CHANGE TO DETERMINE CONTEXT

(71) Applicant: OrCam Technologies Ltd., Jerusalem (IL)

(72) Inventors: Yonatan Wexler, Jerusalem (IL); Amnon Shashua, Mevasseret Zion (IL)

(73) Assignee: ORCAM TECHNOLOGIES LTD., Jerusalem (IL)

(*) Notice: Subject to any disclaimer, the term of this patent is extended or adjusted under 35 U.S.C. 154(b) by 0 days.

This patent is subject to a terminal disclaimer.

(21) Appl. No.: 16/437,820

(22) Filed: Jun. 11, 2019

(65) Prior Publication Data

US 2019/0294909 A1 Sep. 26, 2019

Related U.S. Application Data

(63) Continuation of application No. 14/137,522, filed on Dec. 20, 2013, now Pat. No. 10,339,406.
(Continued)

(51) Int. Cl.
*G06K 9/32* (2006.01)
*G06K 9/00* (2006.01)
(Continued)

(52) U.S. Cl.
CPC ............ *G06K 9/3275* (2013.01); *A61F 9/08* (2013.01); *G06F 3/011* (2013.01); *G06F 3/16* (2013.01);
(Continued)

(58) Field of Classification Search
CPC ........... A61F 9/08; G01B 11/24; G02C 11/10; G06F 17/2765; G06F 3/011; G06F 3/16;
(Continued)

(56) References Cited

U.S. PATENT DOCUMENTS 5,742,264 A 4/1998 Inagaki et al.
6,115,482 A 9/2000 Sears et al.
(Continued)

FOREIGN PATENT DOCUMENTS

EP 2065871 B1 6/2009
EP 2490155 A1 8/2012

OTHER PUBLICATIONS

European Patent Office, PCT International Search Report, International Application No. PCT/IB2014/001252, dated Oct. 14, 2014, 5 pages.
(Continued)

*Primary Examiner* — Anner N Holder
(74) *Attorney, Agent, or Firm* — Finnegan, Henderson, Farabow, Garrett & Dunner LLP

(57) ABSTRACT

Devices and a method are provided for providing feedback to a user. In one implementation, the method comprises obtaining a plurality of images from an image sensor. The image sensor is configured to be positioned for movement with the user's head. The method further comprises monitoring the images, and determining whether relative motion occurs between a first portion of a scene captured in the plurality of images and other portions of the scene captured in the plurality of images. If the first portion of the scene moves less than at least one other portion of the scene, the method comprises obtaining contextual information from the first portion of the scene. The method further comprises providing the feedback to the user based on at least part of the contextual information.

21 Claims, 25 Drawing Sheets

Related U.S. Application Data

(60) Provisional application No. 61/799,649, filed on Mar. 15, 2013, provisional application No. 61/830,122, filed on Jun. 2, 2013.

(51) Int. Cl.

| | | |
|---|---|---|
| *G06K 9/20* | (2006.01) | |
| *G06K 9/22* | (2006.01) | |
| *G06K 9/30* | (2006.01) | |
| *G06K 9/74* | (2006.01) | |
| *G09B 21/00* | (2006.01) | |
| *H04N 5/225* | (2006.01) | |
| *H04N 5/232* | (2006.01) | |
| *G08B 3/10* | (2006.01) | |
| *G08B 6/00* | (2006.01) | |
| *A61F 9/08* | (2006.01) | |
| *G06F 3/01* | (2006.01) | |
| *G06F 3/16* | (2006.01) | |
| *G06F 17/27* | (2006.01) | |
| *G10L 13/04* | (2013.01) | |
| *G01B 11/24* | (2006.01) | |
| *G02C 11/00* | (2006.01) | |

(52) U.S. Cl.
CPC ..... *G06F 17/2765* (2013.01); *G06K 9/00221* (2013.01); *G06K 9/00288* (2013.01); *G06K 9/00442* (2013.01); *G06K 9/00463* (2013.01); *G06K 9/00469* (2013.01); *G06K 9/00483* (2013.01); *G06K 9/00671* (2013.01); *G06K 9/2081* (2013.01); *G06K 9/22* (2013.01); *G06K 9/325* (2013.01); *G06K 9/3233* (2013.01); *G06K 9/3241* (2013.01); *G06K 9/3283* (2013.01); *G06K 9/74* (2013.01); *G08B 3/10* (2013.01); *G08B 6/00* (2013.01); *G09B 21/00* (2013.01); *G09B 21/001* (2013.01); *G09B 21/003* (2013.01); *G09B 21/006* (2013.01); *G10L 13/043* (2013.01); *H04N 5/2251* (2013.01); *H04N 5/2252* (2013.01); *H04N 5/23229* (2013.01); *H04N 5/23232* (2013.01); *G01B 11/24* (2013.01); *G02C 11/10* (2013.01); *G06K 9/00852* (2013.01); *G06K 9/30* (2013.01); *G06K 2009/00489* (2013.01); *G06K 2009/2045* (2013.01)

(58) Field of Classification Search
CPC . G06K 2009/00489; G06K 2009/2045; G06K 9/00221; G06K 9/00288; G06K 9/00442; G06K 9/00463; G06K 9/00469; G06K 9/00483; G06K 9/00671; G06K 9/00852; G06K 9/2081; G06K 9/22; G06K 9/30; G06K 9/3233; G06K 9/3241; G06K 9/325; G06K 9/3275; G06K 9/3283; G06K 9/74; G08B 3/10; G08B 6/00; G09B 21/00; G09B 21/001; G09B 21/003; G09B 21/006; G10L 13/043; H04N 5/2251; H04N 5/2252; H04N 5/23229; H04N 5/23232
See application file for complete search history.

(56) References Cited

U.S. PATENT DOCUMENTS

| | | |
|---|---|---|
| 8,630,454 B1 | 1/2014 | Wang et al. |
| 2003/0086061 A1 | 5/2003 | Pfleger |
| 2004/0233192 A1 | 11/2004 | Hopper |
| 2005/0110875 A1 | 5/2005 | Ma et al. |
| 2005/0208457 A1 | 9/2005 | Fink et al. |
| 2006/0017810 A1 | 1/2006 | Kurzweil et al. |
| 2008/0107307 A1 | 5/2008 | Altherr |
| 2009/0087024 A1 | 4/2009 | Eaton et al. |
| 2009/0278766 A1 | 11/2009 | Sako |
| 2010/0073568 A1 | 3/2010 | Van Ostrand et al. |
| 2011/0044537 A1 | 2/2011 | Cobb et al. |
| 2011/0091098 A1 | 4/2011 | Yuille et al. |
| 2012/0045090 A1 | 2/2012 | Bobbitt et al. |
| 2012/0212406 A1 | 8/2012 | Osterhout et al. |
| 2012/0212593 A1 | 8/2012 | Na'aman et al. |
| 2013/0169536 A1 | 7/2013 | Wexler et al. |
| 2013/0187835 A1 | 7/2013 | Vaught et al. |
| 2013/0253980 A1 | 9/2013 | Blom et al. |
| 2013/0271584 A1 | 10/2013 | Wexler et al. |
| 2014/0003654 A1 | 1/2014 | Beaurepaire |
| 2014/0160170 A1 | 6/2014 | Lyons |

OTHER PUBLICATIONS

European Patent Office, Written Opinion of the International Searching Authority, International Application No. PCT/IB2014/001252, dated Oct. 14, 2014, 6 pages.

International Preliminary Report on Patentability dated Sep. 15, 2015, in corresponding international application No. PCT/IB2014/001252, filed Mar. 11, 2014 (6 pages).

Karacs, Kristof et al., "Bionic Eyeglass: An Audio Guide for Visually Impaired," Biomedical Circuits and Systems Conference, 2006, BIOCAS 2006, IEEE, Piscataway, NJ, Nov. 29, 2006, p. 190-193.

Lai, Chin-Lun et al., "An Integrated Portable Vision Assistant Agency for the Visual Impaired People," 2009 IEEE International Conference on Control and Automation, Christchurch, New Zealand, Dec. 9-11, 2009 (6 pages).

U.S. Appl. No. 14/135,727, filed Dec. 20, 2013, entitled "Systems and Method for Audible Facial Recognition."

U.S. Appl. No. 14/135,757, filed Dec. 20, 2013, entitled "Systems and Methods for Automatic Control of a Continuous Action."

U.S. Appl. No. 14/135,762, filed Dec. 20, 2013, entitled "Systems and Methods for Performing a Triggered Action."

U.S. Appl. No. 14/135,775, filed Dec. 20, 2013, entitled "Systems and Methods for Providing Feedback Based on the State of an Object."

U.S. Appl. No. 14/135,859, filed Dec. 20, 2013, entitled "Apparatus Connectable to Glasses."

U.S. Appl. No. 14/135,928, filed Dec. 20, 2013, entitled "Systems and Methods for Processing Images."

U.S. Appl. No. 14/136,438, filed Dec. 20, 2013, entitled "Apparatus, Method, and Computer Readable Medium for Expedited Text Reading Using Staged OCR Technique."

U.S. Appl. No. 14/136,545, filed Dec. 20, 2013, entitled "Apparatus, Method, and Computer Readable Medium for Recognizing Text on a Curved Surface."

U.S. Appl. No. 14/136,876, filed Dec. 20, 2013, entitled "Apparatus and Method for Analyzing Images."

U.S. Appl. No. 14/137,033, filed Dec. 20, 2013, entitled "Apparatus and Method for Providing Failed-Attempt Feedback Using a Camera on Glasses."

U.S. Appl. No. 14/137,263, filed Dec. 20, 2013, entitled "Apparatus and Method for Executing System Commands Based on Captured Image Data."

U.S. Appl. No. 14/137,328, filed Dec. 20, 2013, entitled "Apparatus and Method for Performing Actions Based on Captured Image Data."

U.S. Appl. No. 14/137,373, filed Dec. 20, 2013, entitled "Apparatus and Method for Automatic Action Selection Based on Image Context."

U.S. Appl. No. 14/137,384, filed Dec. 20, 2013, entitled "Systems and Methods for Audibly Presenting Textual Information Included in Image Data."

U.S. Appl. No. 14/137,446, filed Dec. 20, 2013, entitled "Apparatus and Method for Hierarchical Object Identification Using a Camera on Glasses."

(56) References Cited

OTHER PUBLICATIONS

Ziegler et al., "Non-rigid Surface Detection for Gestural Interaction with Applicable Surfaces " *2012 IEEE Applications of Computer Vision (WACV)* Jan. 9, 2012, 73-80.

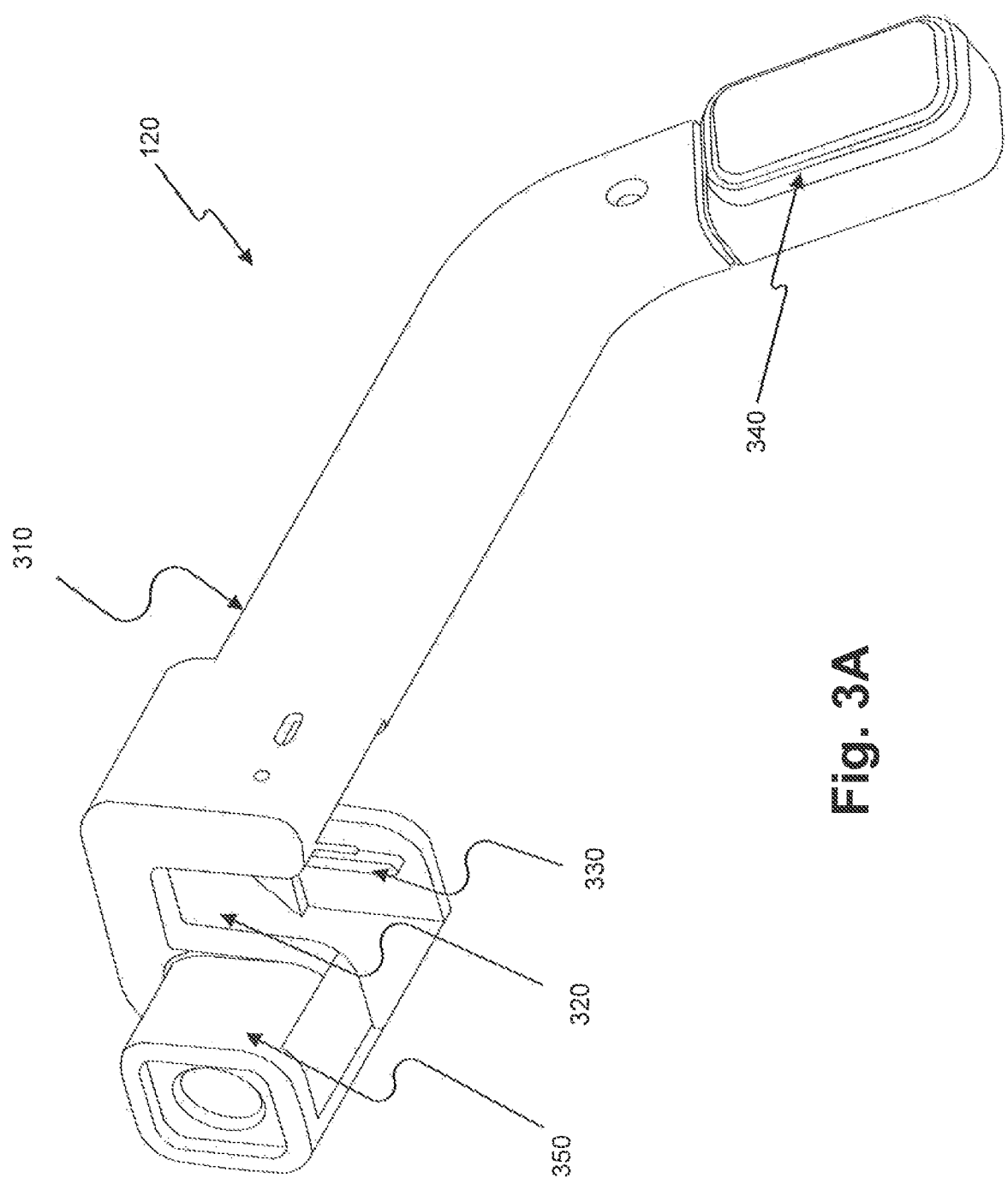

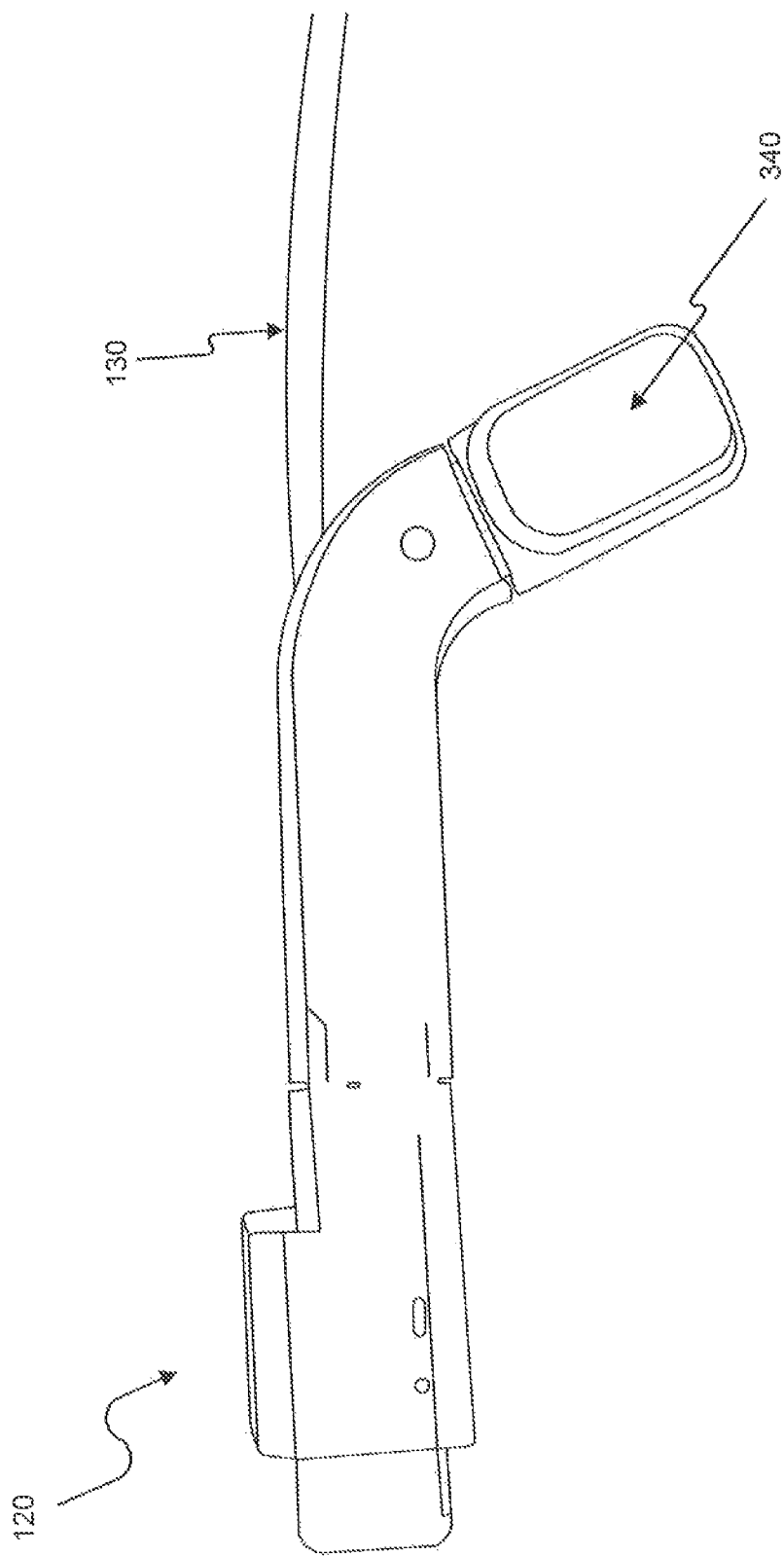

APPARATUS AND METHOD FOR USING BACKGROUND CHANGE TO DETERMINE CONTEXT

CROSS REFERENCE TO RELATED APPLICATIONS

This application is a continuation of application Ser. No. 14/137,522, filed Dec. 20, 2013, which claims the benefit of priority of U.S. Provisional Patent Application No. 61/799,649, filed on Mar. 15, 2013, and U.S. Provisional Patent Application No. 61/830,122, filed on Jun. 2, 2013. The foregoing applications are incorporated herein by reference in their entireties.

BACKGROUND

I. Technical Field

This disclosure generally relates to devices and methods for providing information to a user. More particularly, this disclosure relates to devices and methods for providing information to a user by processing images captured from the environment of the user.

II. Background Information

Visual acuity is an indication of the clarity or clearness of a person's vision that is commonly measured twenty feet from an object. When measuring visual acuity, the ability of a person to identify black symbols on a white background at twenty feet is compared to the ability of a person with normal eyesight. This comparison can be symbolized by a ratio. For example, a ratio of 20/70 vision means a person located at a distance of twenty feet can see what a person with normal vision can see at seventy feet. A person has low vision if he or she has a visual acuity between 20/70 and 20/200 in the better-seeing eye that cannot be corrected or improved with regular eyeglasses. The prevalence of low vision is about one in a hundred for people in their sixties and rapidly increases to one in five for people in their nineties. Low vision may also depend on the environment. For example, some individuals may be able to see only when there is ample light.

A person may have low vision (also known as visual impairment) for several reasons. Other than eye damage and failure of the brain to receive visual cues sent by the eyes, different medical conditions may cause visual impairment. Medical conditions that may cause visual impairment include Age-related Macular Degeneration (AMD), retinitis pigmentosa, cataract, and diabetic retinopathy.

AMD, which usually affects adults, is caused by damage to the retina that diminishes vision in the center of a person's visual field. The lifetime risk for developing AMD is strongly associated with certain genes. For example, the lifetime risk of developing AMD is 50% for people that have a relative with AMD, versus 12% for people that do not have relatives with AMD.

Retinitis pigmentosa is an inherited, degenerative eye disease that causes severe vision impairment and often blindness. The disease process begins with changes in pigment and damage to the small arteries and blood vessels that supply blood to the retina. There is no cure for retinitis pigmentosa and no known treatment can stop the progressive vision loss caused by the disease.

A cataract is a clouding of the lens inside the eye which leads to a decrease in vision. Over time, a yellow-brown pigment is deposited within the lens and obstructs light from passing and being focused onto the retina at the back of the eye. Biological aging is the most common cause of a cataract, but a wide variety of other risk factors (e.g., excessive tanning, diabetes, prolonged steroid use) can cause a cataract.

Diabetic retinopathy is a systemic disease that affects up to 80% of all patients who have had diabetes for ten years or more. Diabetic retinopathy causes microvascular damage to a blood-retinal barrier in the eye and makes the retinal blood vessels more permeable to fluids.

People with low vision experience difficulties due to lack of visual acuity, field-of-view, color perception, and other visual impairments. These difficulties affect many aspects of everyday life. Persons with low vision may use magnifying glasses to compensate for some aspects of low vision. For example, if the smallest letter a person with 20/100 vision can read is five times larger than the smallest letter that a person with 20/20 vision can read, then 5× magnification should make everything that is resolvable to the person with 20/20 vision resolvable to the person with low vision. However, magnifying glasses are expensive and cannot remedy all aspects of low vision. For example, a person with low vision who wears magnifying glasses may still have a difficult time recognizing details from a distance (e.g., people, signboards, traffic lights, etc.). Accordingly, there is a need for other technologies that can assist people who have low vision accomplish everyday activities.

SUMMARY

Embodiments consistent with the present disclosure provide devices and methods for providing information to a user by processing images captured from the environment of the user. The disclosed embodiments may assist persons who have low vision.

In accordance with a disclosed embodiment, an apparatus is provided for providing feedback to a user. The apparatus may comprise an image sensor configured to be positioned for movement with a head of the user as the head moves, and to capture real time images from an environment of the user, and at least one processor device for determining contextual information based on the real time images. The processor device may be configured to monitor a plurality of images captured by the image sensor to determine whether relative motion occurs between a first portion of a scene captured in the plurality of images and other portions of the scene captured in the plurality of images. Further, if the first portion of the scene moves less than at least one other portion of the scene, the processor device may be configured to obtain contextual information from the first portion of the scene. Also, the processor device may be configured to provide the feedback to the user based on at least part of the contextual information.

In accordance with another disclosed embodiment, an apparatus is provided for providing feedback to a user. The apparatus may comprise an image sensor for capturing real time images from an environment of the user. The image sensor may be configured to be positioned for movement with a head of the user as the head moves such that an aiming direction of the image sensor falls within a field of view of the user. The apparatus may further comprise at least one processor device for determining contextual information based on the real time images. The processor device may be configured to monitor the real time images captured by the image sensor to automatically determine whether an object in the user's field of view lingers within a plurality of the real time images. Additionally, the processor device may be configured to identify at least one object determined to linger within the plurality of real time images as an object of interest. The processor device may be configured to obtain contextual information associated with the object of interest. The processor device may be further configured to provide the feedback to the user based on at least part of the contextual information.

In accordance with yet another disclosed embodiment, a method is provided for providing feedback to a user. The method comprises obtaining from an image sensor a plurality of images. The image sensor is configured to be positioned for movement with a head of the user. The method further comprises monitoring the plurality of images captured by the image sensor. Further, the method comprises determining whether relative motion occurs between a first portion of a scene captured in the plurality of images and other portions of the scene captured in the plurality of images. Also, if the first portion of the scene moves less than the at least one other portion of the scene, the method comprises obtaining contextual information from the first portion of the scene. The method further comprises providing the feedback to the user based on at least part of the contextual information.

In accordance with still another disclosed embodiment, an apparatus is provided for processing real time images of an environment of a user. The apparatus may comprise a camera including an image sensor configured to be positioned for movement with a head of the user as the head moves, and to capture real time images. The apparatus may further comprise at least one processor device for determining contextual information based on the real time images. The processor device may be configured to monitor a plurality of images captured by the image sensor to determine whether relative motion occurs between a first portion of a scene captured in the plurality of images and other portions of the scene captured in the plurality of images. Additionally, if the first portion of the scene moves less than at least one other portion of the scene, the processor device may be configured to obtain contextual information from the first portion of the scene. The processor device may be further configured to adjust at least one parameter associated with the camera based on at least part of the contextual information.

Consistent with other disclosed embodiments, non-transitory computer-readable storage media may store program instructions, which are executed by at least one processor device and perform any of the methods described herein.

The foregoing general description and the following detailed description are exemplary and explanatory only and are not restrictive of the claims.

BRIEF DESCRIPTION OF THE DRAWINGS

The accompanying drawings, which are incorporated in and constitute a part of this disclosure, illustrate various disclosed embodiments. In the drawings:

FIG. 3A is a schematic illustration of an example of a sensory unit from a first viewpoint;

FIG. 3D is a schematic illustration of the sensory unit shown in FIG. 3A from a fourth viewpoint;

DETAILED DESCRIPTION

Figure 1:
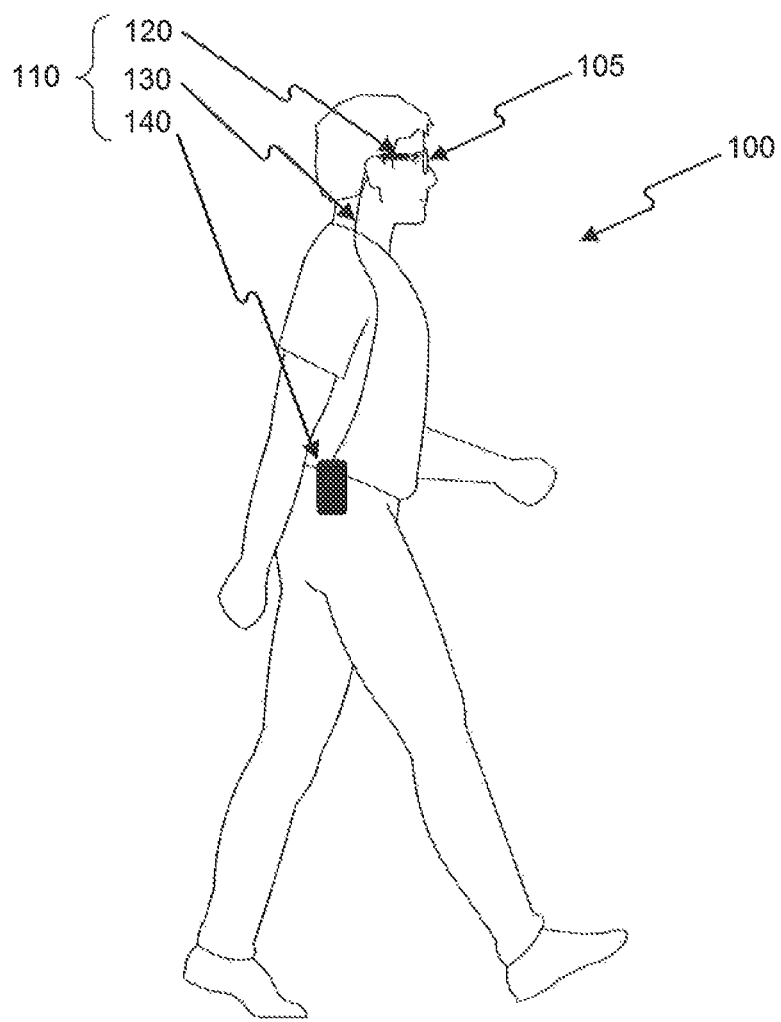
FIG. 1 is a schematic illustration of a user wearing an apparatus for aiding persons who have low vision.

The following detailed description refers to the accompanying drawings. Wherever possible, the same reference numbers are used in the drawings and the following description to refer to the same or similar parts. While several illustrative embodiments are described herein, modifications, adaptations and other implementations are possible. For example, substitutions, additions or modifications may be made to the components illustrated in the drawings, and the illustrative methods described herein may be modified by substituting, reordering, removing, or adding steps to the disclosed methods. Accordingly, the following detailed description is not limited to the disclosed embodiments and examples. Instead, the proper scope is defined by the appended claims.

Disclosed embodiments provide devices and methods for assisting people who have low vision. One example of the disclosed embodiments is a device that includes a camera configured to capture real-time image data from the environment of the user. The device also includes a processing unit configured to process the real-time image data and provide real-time feedback to the user. The real-time feedback may include, for example, an output that audibly identifies individuals from a distance, reads signboards, and/or identifies the state of a traffic light.

FIG. 1 illustrates a user 100 wearing an apparatus 110 connected to glasses 105, consistent with a disclosed embodiment. Apparatus 110 may provide functionality for aiding user 100 with various daily activities that are otherwise difficult for user 100 to accomplish due to low vision. Glasses 105 may be prescription glasses, magnifying glasses, non-prescription glasses, safety glasses, sunglasses, etc.

As shown in FIG. 1, apparatus 110 includes a sensory unit 120 and a processing unit 140. Sensory unit 120 may be connected to a support (not shown in FIG. 1) that is mounted on glasses 105, In addition, sensory unit 120 may include an image sensor (not shown in FIG. 1) for capturing real-time image data of the field-of-view of user 100. The term "image data" includes any form of data retrieved from optical signals in the near-infrared, infrared, visible, and ultraviolet spectrums. The image data may be used to form video clips and/or photographs.

Processing unit 140 may communicate wirelessly or via a wire 130 connected to sensory unit 120. In some embodiments, processing unit 140 may produce an output of audible feedback to user 100 (e.g., using a speaker or a bone conduction headphone).

Apparatus 110 is one example of a device capable of implementing the functionality of the disclosed embodiments. Other devices capable of implementing the disclosed embodiments include, for example, a mobile computer with a camera (e.g., a smartphone, a smartwatch, a tablet, etc.) or a clip-on-camera configured to communicate with a processing unit (e.g., a smartphone or a dedicated processing unit, which can be carried in a pocket). A person skilled in the art will appreciate that different types of devices and arrangements of devices may implement the functionality of the disclosed embodiments.

Figure 2A:
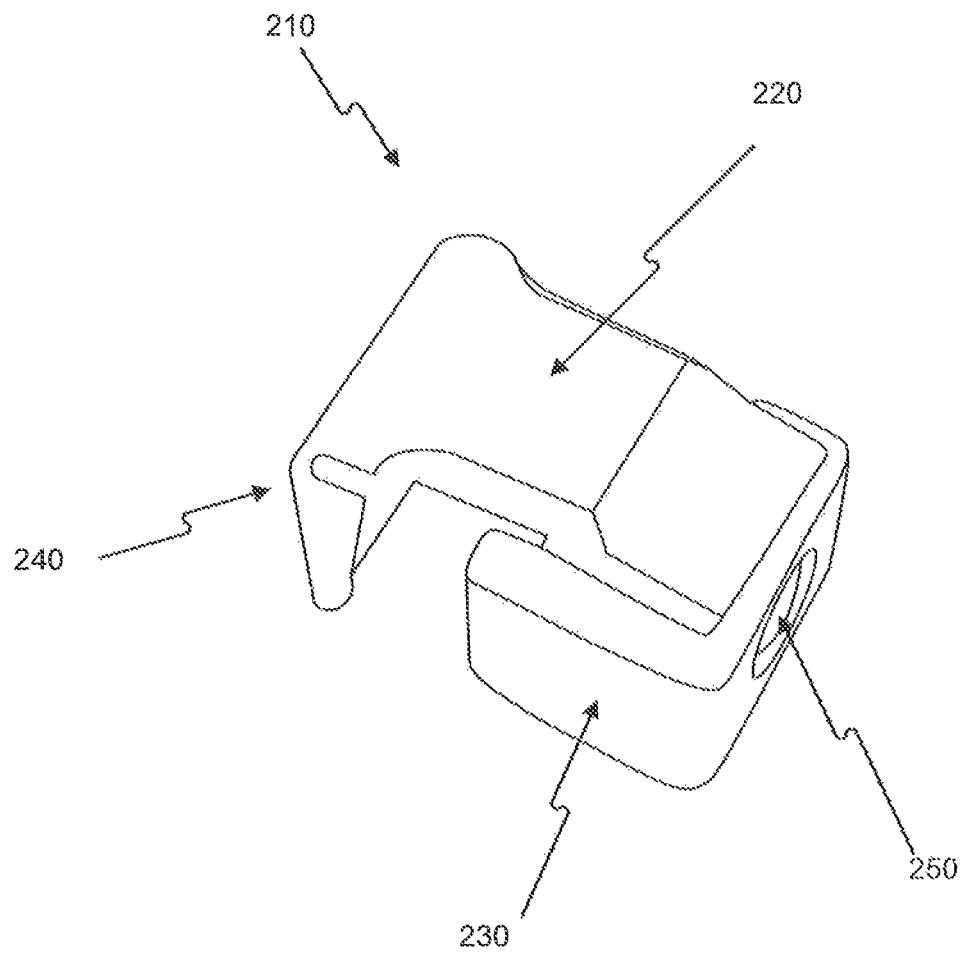
FIG. 2A is a schematic illustration of an example of a support from a first viewpoint.

FIG. 2A is a schematic illustration of an example of a support 210. As discussed in connection with FIG. 1, support 210 may be mounted on glasses 105 and connect to sensory unit 120. The term "support" includes any device or structure that enables detaching and reattaching of a device including a camera to a pair of glasses or to another object (e.g., a helmet). Support 210 may be made from plastic (e.g., polycarbonate), metal (e.g., aluminum), or a combination of plastic and metal (e.g., carbon fiber graphite). Support 210 may be mounted on glasses 105 using screws, bolts, snaps, or any fastening means used in the art.

As shown in FIG. 2A, support 210 includes a base 230 connected to a clamp 240. A bridge 220 connects base 230 with clamp 240. Base 230 and clamp 240 enable sensory unit 120 to easily attach to and detach from support 210. In one embodiment, base 230 may include an internally threaded member 250 for cooperating with a screw (not shown in FIG. 2A) to mount support 210 on glasses 105.

Figure 2B:
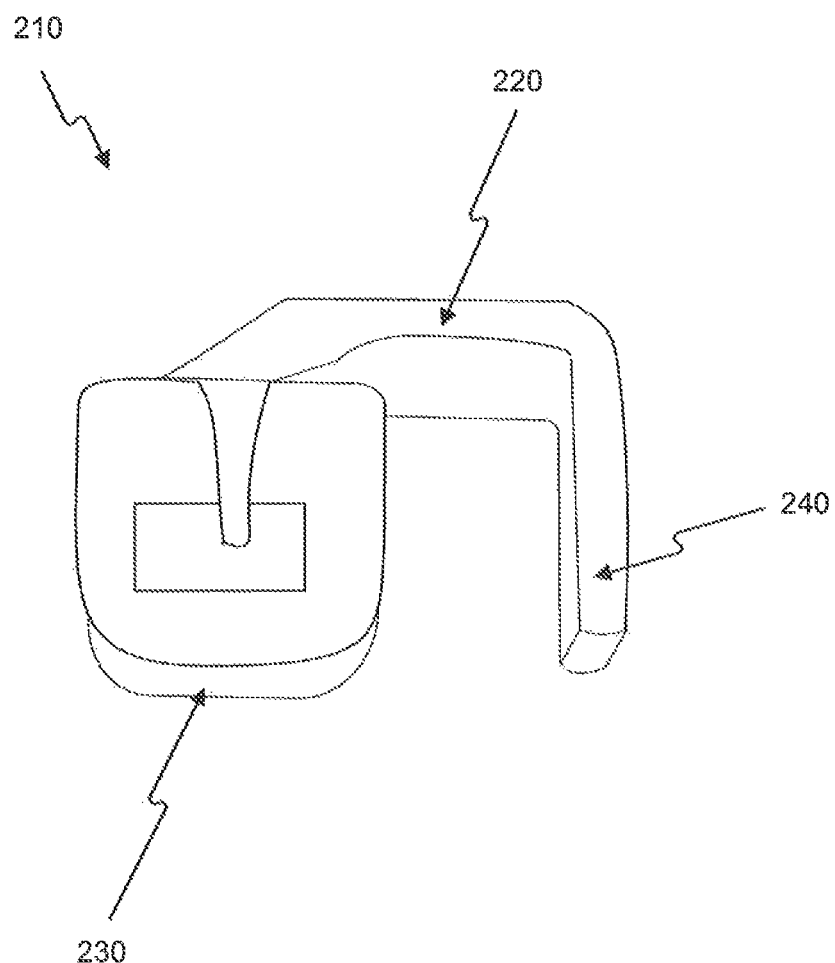
FIG. 2B is a schematic illustration of the support shown in FIG. 2A from a second viewpoint.

FIG. 2B illustrates support 210 from a second viewpoint. The viewpoint shown in FIG. 2B is from a side orientation of support 210.

Figure 2C:
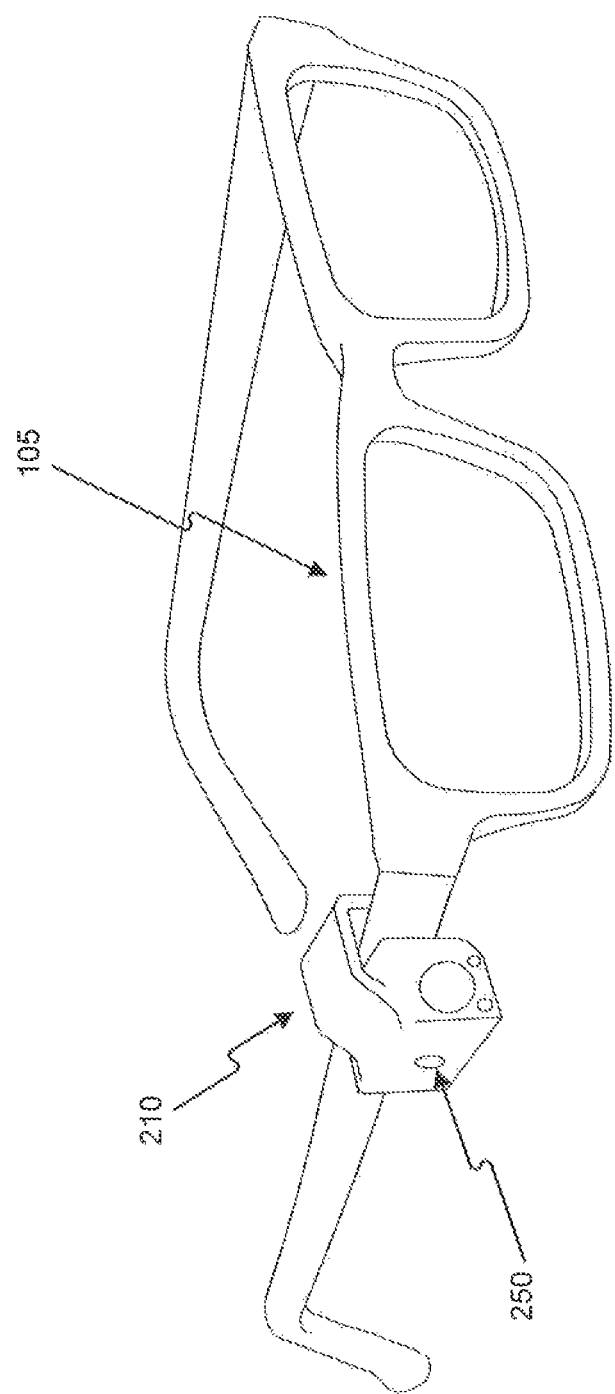
FIG. 2C is a schematic illustration of the support shown in FIG. 2A mounted on a pair of glasses.

FIG. 2C illustrates support 210 mounted on glasses 105. Support 210 may be configured for mounting on any kind of glasses (e.g., eyeglasses, sunglasses, 3D glasses, safety glasses, etc.). As shown in FIG. 2C, sensory unit 120 is not attached to support 210 and, accordingly, support 210 may be sold separately from apparatus 110. This arrangement makes apparatus 110 compatible with a variety of glasses. For example, some users may have several pairs of glasses and may wish to mount a support on each pair of glasses.

In other embodiments, support 210 may be an integral part of a pair of glasses, or sold and installed by an optometrist. For example, support 210 may be configured for mounting on the arms of glasses 105 near the frame front, but before the hinge. Alternatively, support 210 may be configured for mounting on the bridge of glasses 105.

Figure 2D:
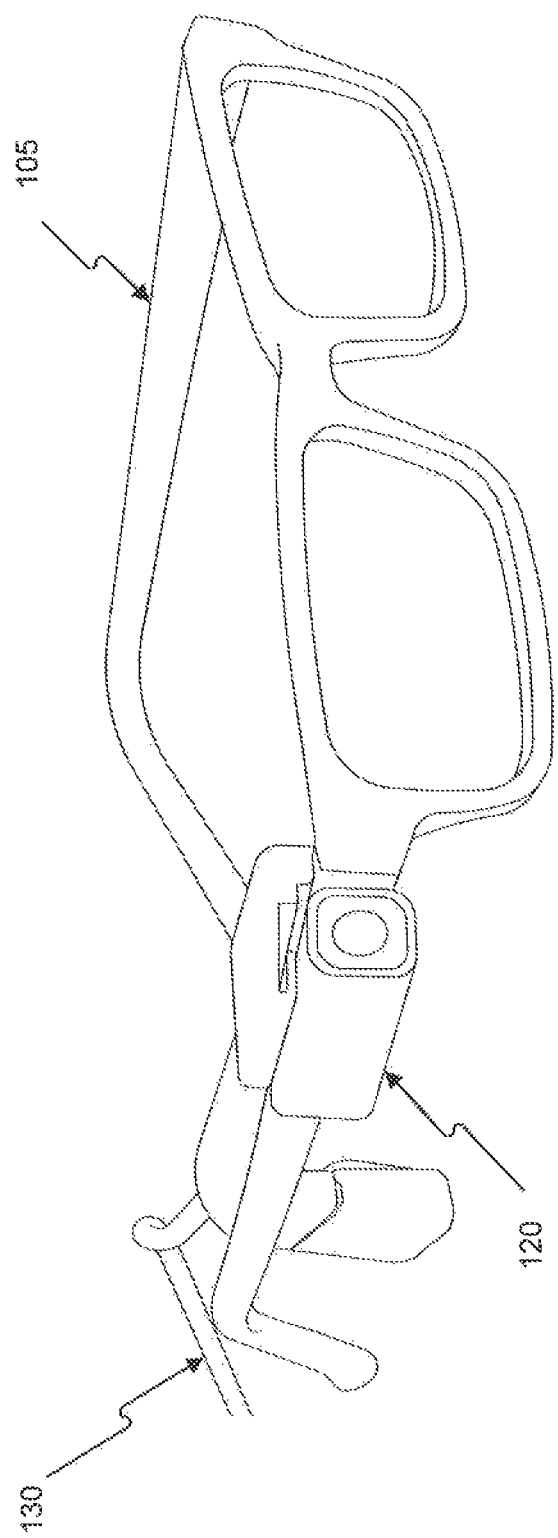
FIG. 2D is a schematic illustration of a sensory unit attached to the support that is mounted on the pair of glasses shown in FIG. 2C.

FIG. 2D illustrates sensory unit 120 attached to support 210 (not visible in FIG. 2D), and support 210 mounted on glasses 105. In some embodiments, support 210 may include a quick release mechanism for disengaging and reengaging sensory unit 120. For example, support 210 and sensory unit 120 may include magnetic elements. As an alternative example, support 210 may include a male latch member and sensory unit 120 may include a female receptacle.

When sensory unit 120 is attached (or reattached) to support 210, the field-of-view of a camera associated with sensory unit 120 may be substantially identical to the field-of-view of user 100. Accordingly, in some embodiments, after support 210 is attached to sensory unit 120, directional calibration of sensory unit 120 may not be required because sensory unit 120 aligns with the field-of-view of user 100.

In other embodiments, support 210 may include an adjustment component (not shown in FIG. 2D) to enable calibration of the aiming direction of sensory unit 120 in a substantially set position that is customized to user 100 wearing glasses 105. For example, the adjustment component may include an adjustable hinge to enable vertical and horizontal alignment of the aiming direction of sensory unit 120. Adjusting the alignment of sensory unit 120 may assist users who have a unique and individual visual impairment. The adjustment may be internal or external to sensory unit 120.

Figure 2E:
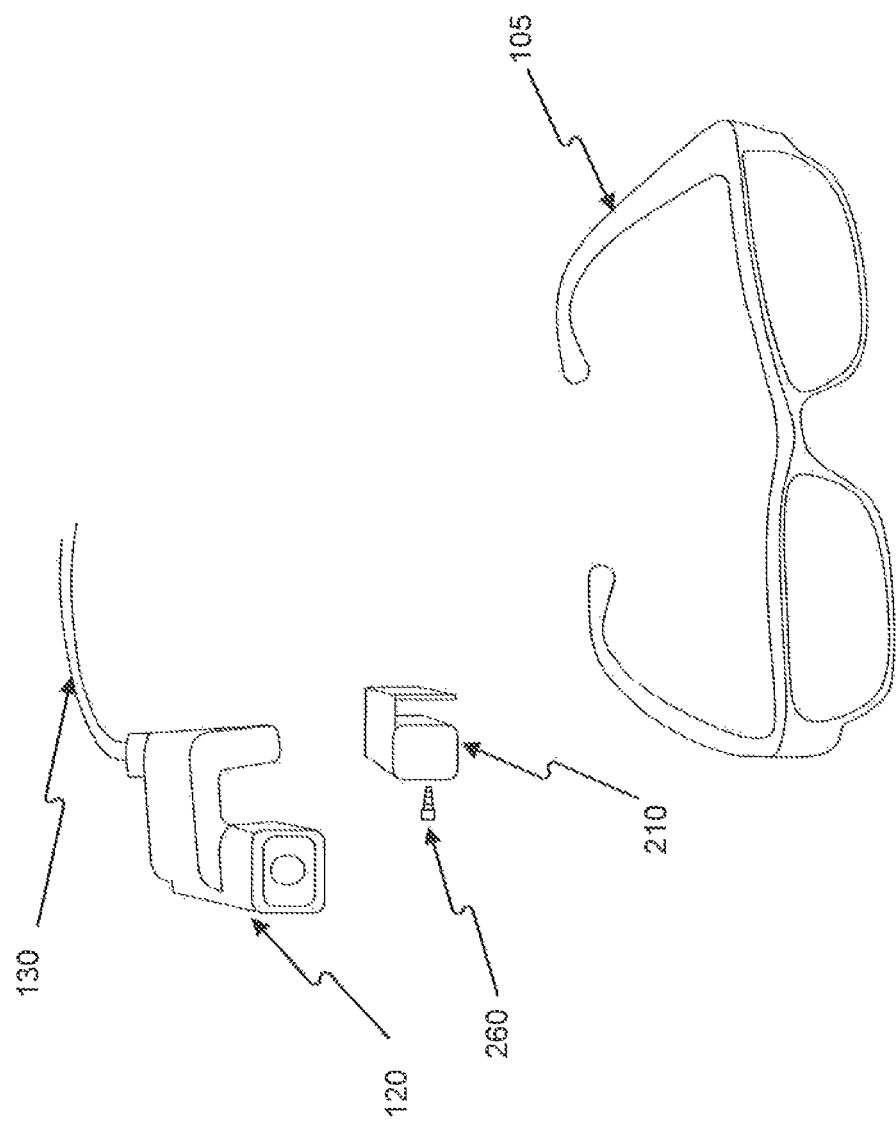
FIG. 2E is an exploded view of FIG. 2D.

FIG. 2E is an exploded view of the components shown in FIG. 2D. Sensory unit 120 may be attached to glasses 105 in the following way. Initially, support 210 may be mounted on glasses 105 using screw 260. Next, screw 260 may be inserted into internally threaded member 250 (not shown in FIG. 2E) in the side of support 210. Sensory unit 120 may then be clipped on support 210 such that it is aligned with the field-of-view of user 100.

FIG. 3A is a schematic illustration of sensory unit 120 from a first viewpoint. As shown in FIG. 3A, sensory unit 120 includes a feedback-outputting unit 340 and an image sensor 350.

Sensory unit 120 is configured to cooperate with support 210 using clip 330 and groove 320, which fits the dimensions of support 210. The term "sensory unit" refers to any electronic device configured to capture real-time images and provide a non-visual output. Furthermore, as discussed above, sensory unit 120 includes feedback-outputting unit 340. The term "feedback-outputting unit" includes any device configured to provide information to a user.

In some embodiments, feedback-outputting unit 340 may be configured to be used by blind persons and persons with low vision. Accordingly, feedback-outputting unit 340 may be configured to output nonvisual feedback. The term "feedback" refers to any output or information provided in response to processing at least one image in an environment. For example, feedback may include a descriptor of a branded product, an audible tone, a tactile response, and/or information previously recorded by user 100. Furthermore, feedback-outputting unit 340 may comprise appropriate components for outputting acoustical and tactile feedback that people with low vision can interpret. For example, feedback-outputting unit 340 may comprise audio headphones, a speaker, a bone conduction headphone, interfaces that provide tactile cues, vibrotactile stimulators, etc.

As discussed above, sensory unit 120 includes image sensor 350. The term "image sensor" refers to a device capable of detecting and converting optical signals in the near-infrared, infrared, visible, and ultraviolet spectrums into electrical signals. The electric signals may be used to form an image based on the detected signal. For example, image sensor 350 may be part of a camera. In some embodiments, when sensory unit 120 is attached to support 210, image sensor 350 may acquire a set aiming direction without the need for directional calibration. The set aiming direction of image sensor 350 may substantially coincide with the field-of-view of user 100 wearing glasses 105. For example, a camera associated with image sensor 350 may be installed within sensory unit 120 in a predetermined angle in a position facing slightly downwards (e.g., 5-15 degrees from the horizon). Accordingly, the set aiming direction of image sensor 350 may match the field-of-view of user 100.

As shown in FIG. 3A, feedback-outputting unit 340 and image sensor 350 are included in a housing 310. The term "housing" refers to any structure that at least partially covers, protects, or encloses a sensory unit. The housing may be made from one or more different materials (e.g., plastic or aluminum). In one embodiment, housing 310 may be designed to engage with a specific pair of glasses having a specific support (e.g., support 210). In an alternative embodiment, housing 310 may be designed to engage more than one pair of glasses, each having a support (e.g., support 210) mounted thereon. Housing 310 may include a connector for receiving power from an external mobile-power-source or an internal mobile-power-source, and for providing an electrical connection to image sensor 350.

Figure 3B:
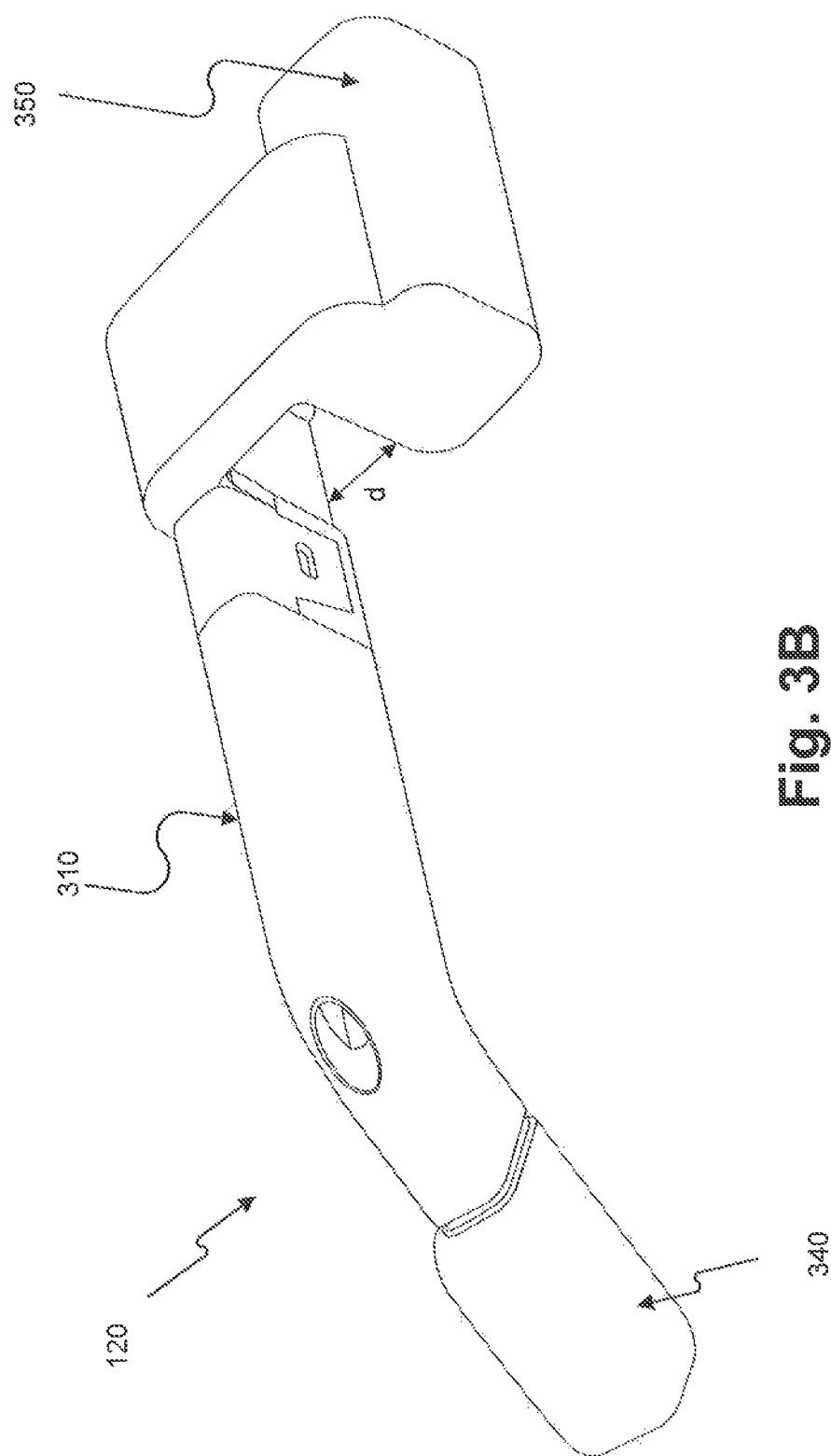
FIG. 3B is a schematic illustration of the sensory unit shown in FIG. 3A from a second viewpoint.

FIG. 3B is a schematic illustration of sensory unit 120 from a second viewpoint. As shown in FIG. 3B, housing 310 includes a U-shaped element. An inner distance "d" between each side of the U-shaped element is larger than the width of the arm of glasses 105. Additionally, the inner distance "d" between each side of the U-shaped element is substantially equal to a width of support 210. The inner distance "d" between each side of the U-shaped element may allow user 100 to easily attach housing 310 to support 210, which may be mounted on glasses 105. As illustrated in FIG. 3B, image sensor 350 is located on one side of the U-shaped element and feedback-outputting unit 340 is located on another side of the U-shaped element.

Figure 3C:
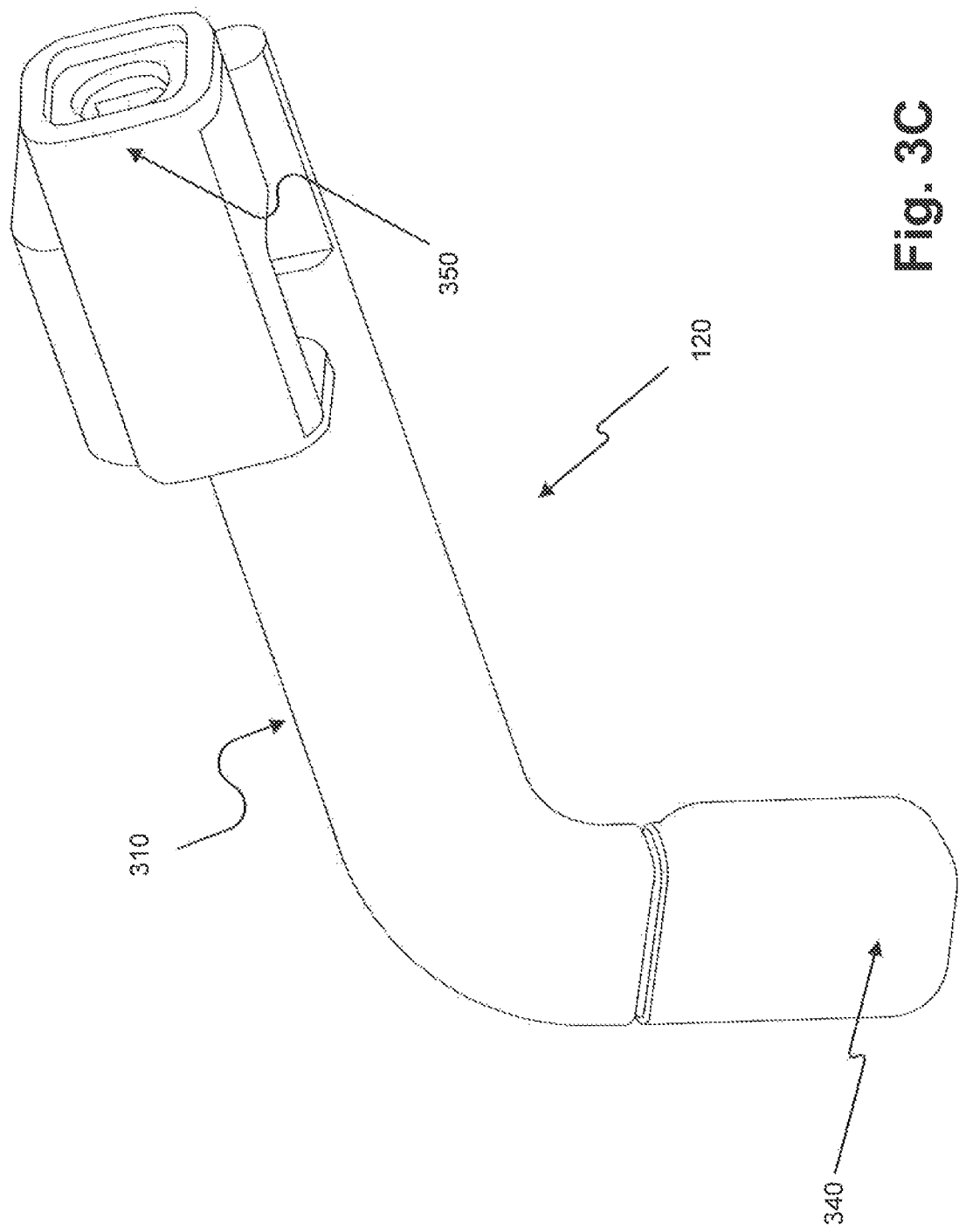
FIG. 3C is a schematic illustration of the sensory unit shown in FIG. 3A from a third viewpoint.

FIG. 3C is a schematic illustration of sensory unit 120 from a third viewpoint. The viewpoint shown in FIG. 3C is from a side orientation of sensory unit 120 and shows the side of the U-shaped element that includes image sensor 350.

FIG. 3D is a schematic illustration of sensory unit 120 from a fourth viewpoint. The viewpoint shown in FIG. 3D is from an opposite side of the orientation shown in FIG. 3C. FIG. 3D shows the side of the U-shaped element that includes feedback-outputting unit 340.

Figure 3E:
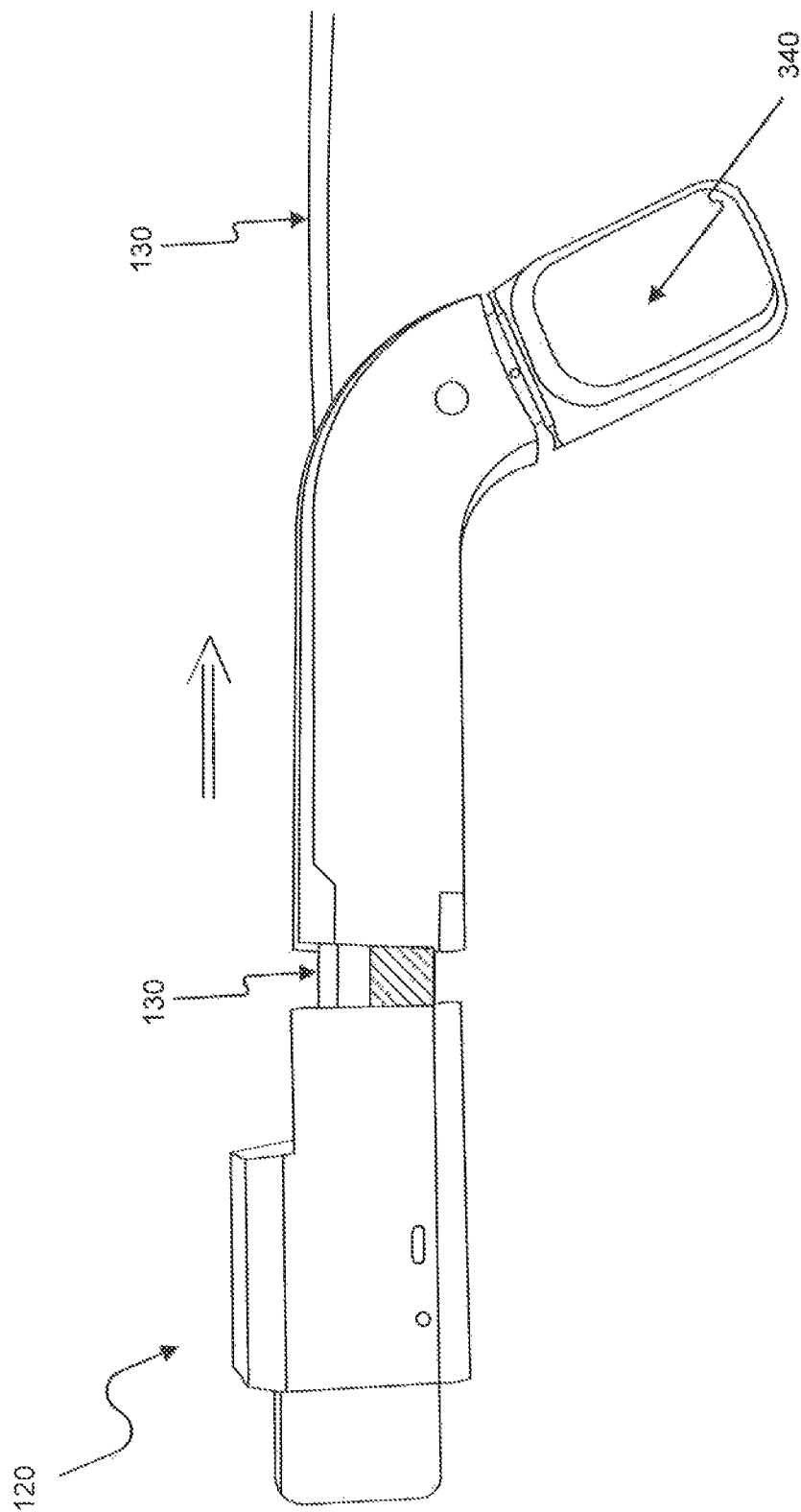
FIG. 3E is a schematic illustration of the sensory unit shown in FIG. 3A in an extended position.

FIG. 3E is a schematic illustration of the sensory unit shown in FIG. 3A in an extended position. As shown in FIG. 3E, a portion of sensory unit 120 is extendable and wire 130 may pass through a channel of sensory unit 120. This arrangement may allow a user to adjust the length and the angle of sensory unit 120 without interfering with the operation of apparatus 110.

User 100 may adjust the U-shaped element of sensory unit 120 so that feedback-outputting unit 340 is positioned adjacent to the user's ear or the user's temple. Accordingly, sensory unit 120 may be adjusted for use with different users who may have different head sizes. Alternatively, a portion of sensory unit 120 may be flexible such that the angle of feedback-outputting unit 340 is relative to the user's ear or the user's temple.

Figure 4A:
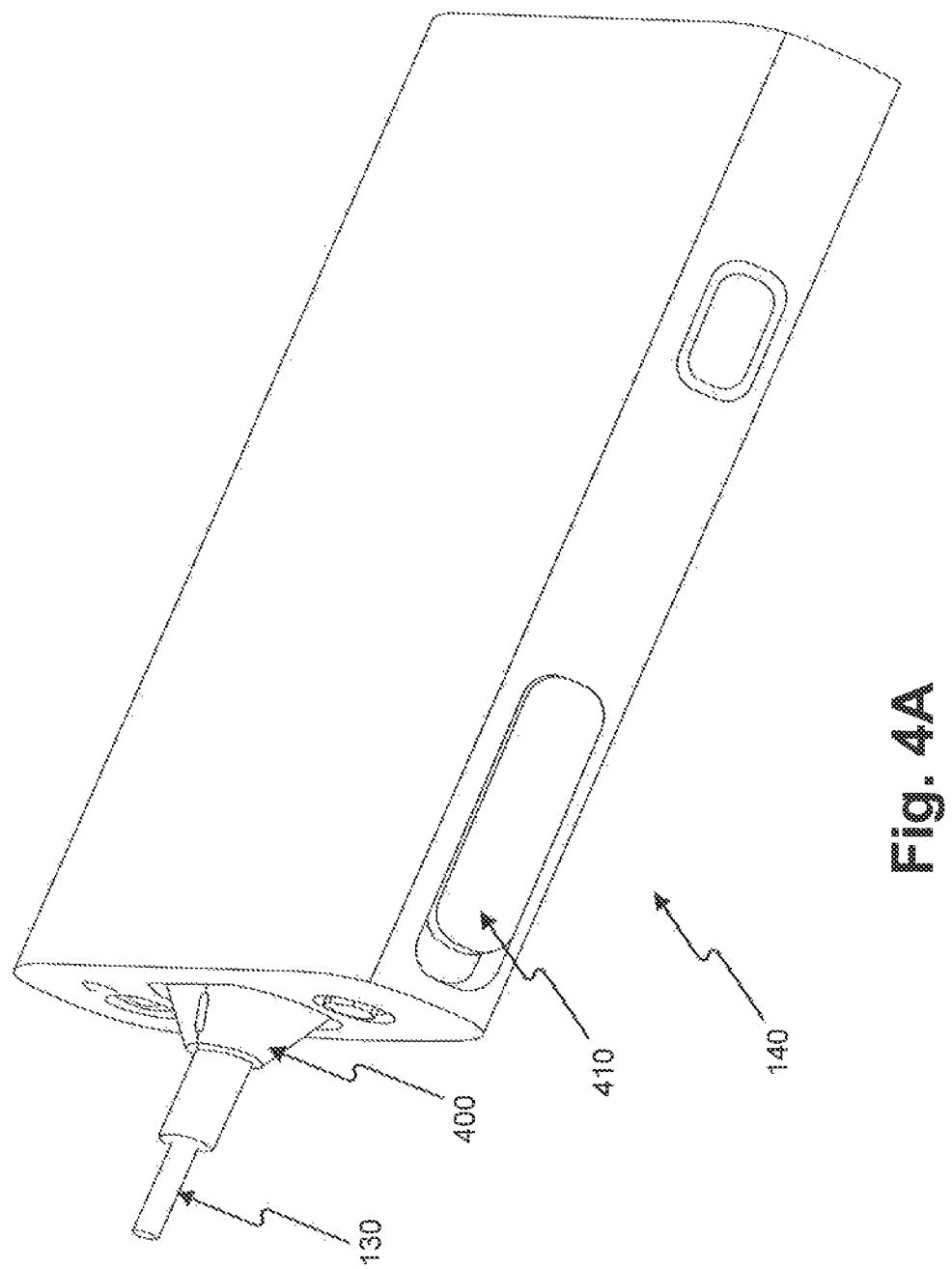
FIG. 4A is a schematic illustration of an example of a processing unit from a first viewpoint.

FIG. 4A is a schematic illustration of processing unit 140. As shown in FIG. 4A, processing unit 140 has a rectangular shape, which easily fits in a pocket of user 100. Processing unit 140 includes a connector 400 for connecting wire 130 to processing unit 140. Wire 130 may be used to transmit power from processing unit 140 to sensory unit 120, and data to and from processing unit 140 to sensory unit 120. Alternatively, wire 130 may comprise multiple wires (e.g., a wire dedicated to power transmission and a wire dedicated to data transmission).

Processing unit 140 includes a function button 410 for enabling user 100 to provide input to apparatus 110. Function button 410 may accept different types of tactile input (e.g., a tap, a click, a double-click, a long press, a right-to-left slide, a left-to-right slide). In some embodiments, each type of input may be associated with a different action. For example, a tap may be associated with the function of confirming an action, while a right-to-left slide may be associated with the function of repeating the last output.

Figure 4B:
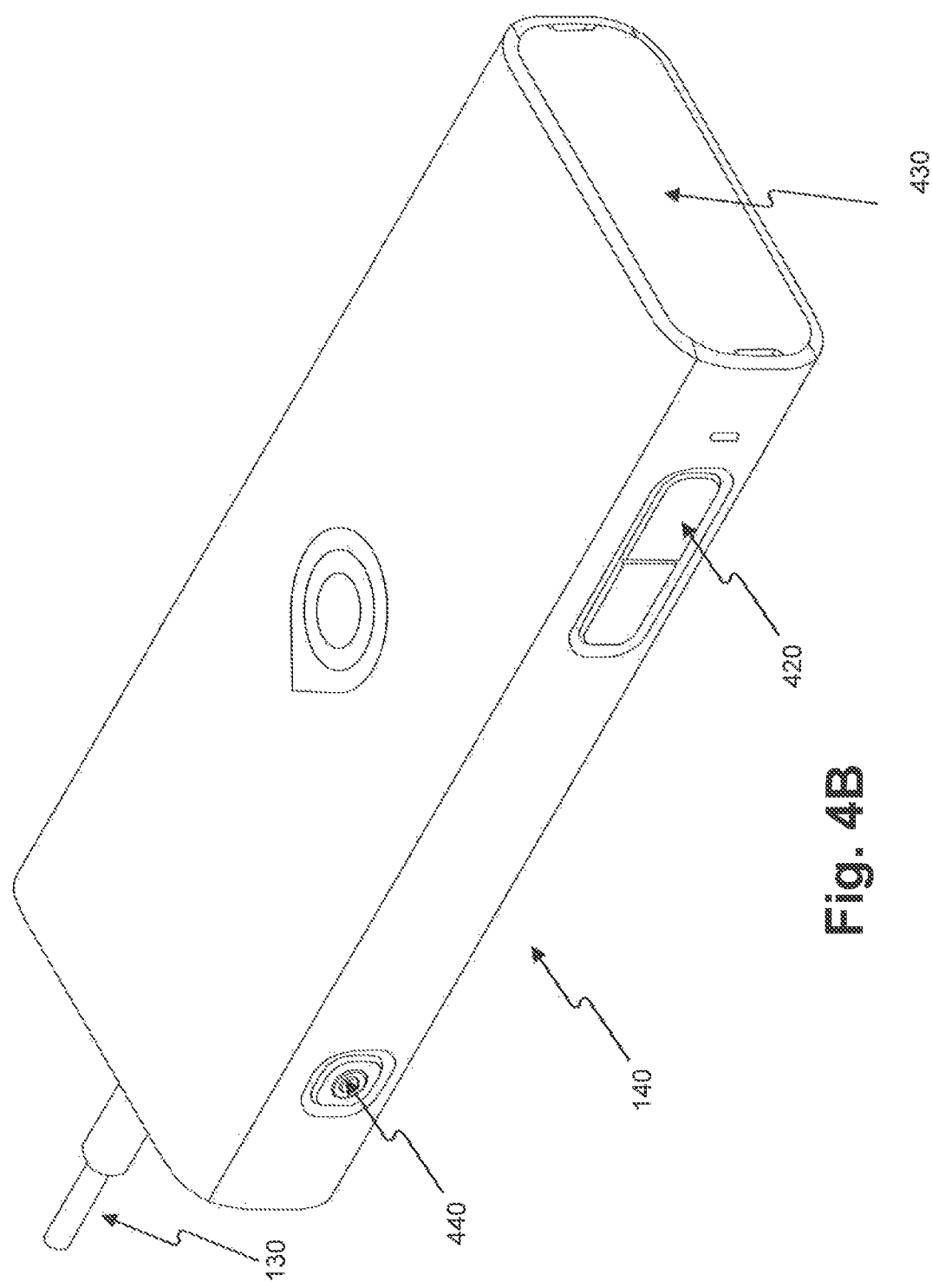
FIG. 4B is a schematic illustration of the processing unit shown in FIG. 4A from a second viewpoint.

FIG. 4B is a schematic illustration of processing unit 140 from a second viewpoint. As shown in FIG. 4B, processing unit 140 includes a volume switch 420, a battery pack compartment 430, and a power port 440. In one embodiment, user 100 may charge apparatus 110 using a charger connectable to power port 440. Alternatively, user 100 may replace a battery pack (not shown) stored in battery pack compartment 430.

Figure 5A:
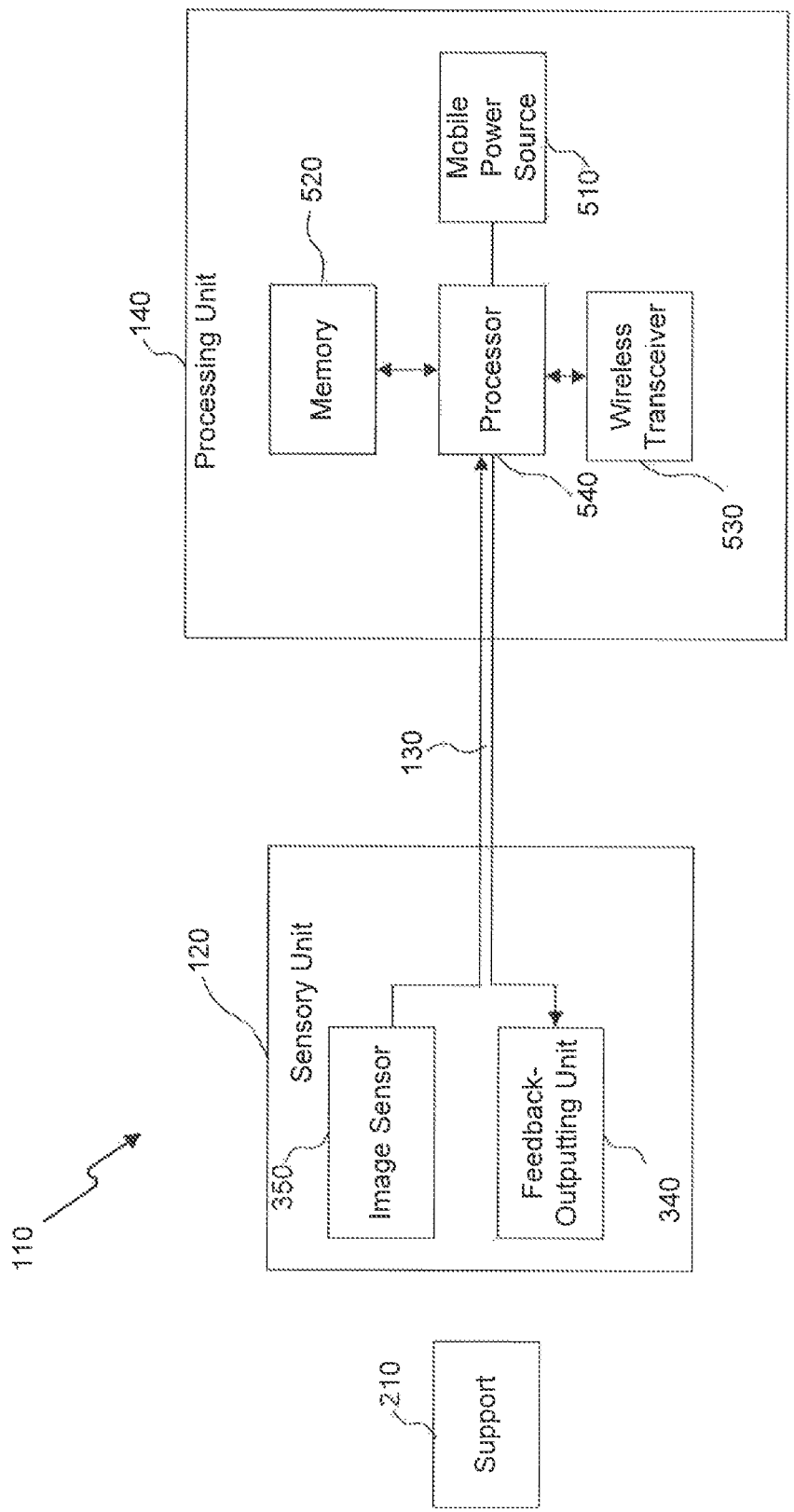
FIG. 5A is a block diagram illustrating an example of the components of an apparatus for aiding persons who have low vision according to a first embodiment.

FIG. 5A is a block diagram illustrating the components of apparatus 110 according to a first embodiment. Specifically, FIG. 5A depicts an embodiment in which apparatus 110 comprises sensory unit 120 and processing unit 140, as discussed in connection with, for example, FIG. 1. Furthermore, sensory unit 120 may be physically coupled to support 210.

As shown in FIG. 5A, sensory unit 120 includes feedback-outputting unit 340 and image sensor 350. Although one image sensor is depicted in FIG. 5A, sensory unit 120 may include a plurality of image sensors (e.g., two image sensors). For example, in an arrangement with more than one image sensor, each of the image sensors may be face a different direction or be associated with a different camera (e.g., a wide angle camera, a narrow angle camera, an IR camera, etc.). In other embodiments (not shown in the figure) sensory unit 120 may also include buttons and other sensors such as a microphone and inertial measurements devices.

As further shown in FIG. 5A, sensory unit 120 is connected to processing unit 140 via wire 130. Processing unit 140 includes a mobile power source 510, a memory 520, a wireless transceiver 530, and a processor 540.

Processor 540 may constitute any physical device having an electric circuit that performs a logic operation on input or inputs. For example, processor 540 may include one or more integrated circuits, microchips, microcontrollers, microprocessors, all or part of a central processing unit (CPU), graphics processing unit (GPU), digital signal processor (DSP), field-programmable gate array (FPGA), or other circuits suitable for executing instructions or performing logic operations. The instructions executed by processor 540 may, for example, be pre-loaded into a memory integrated with or embedded into processor 540 or may be stored in a separate memory (e.g., memory 520). Memory 520 may comprise a Random Access Memory (RAM), a Read-Only Memory (ROM), a hard disk, an optical disk, a magnetic medium, a flash memory, other permanent, fixed, or volatile memory, or any other mechanism capable of storing instructions.

Although one processor is shown in FIG. 5A, processing unit 140 may include more than one processor. Each processor may have a similar construction or the processors may be of differing constructions that are electrically connected or disconnected from each other. For example, the processors may be separate circuits or integrated in a single circuit. When more than one processor is used, the processors may be configured to operate independently or collaboratively. The processors may be coupled electrically, magnetically, optically, acoustically, mechanically or by other means that permit them to interact.

In some embodiments, processor 540 may change the aiming direction of image sensor 350 using image data provided from image sensor 350. For example, processor 540 may recognize that a user is reading a book and determine that the aiming direction of image sensor 350 is offset from the text. That is, because the words in the beginning of each line of text are not fully in view, processor 540 may determine that image sensor 350 is tilted down and to the right. Responsive thereto, processor 540 may adjust the aiming direction of image sensor 350.

Processor 540 may access memory 520. Memory 520 may be configured to store information specific to user 100. For example, data for image representations of known individuals, favorite products, personal items, etc., may be stored in memory 520. In one embodiment, user 100 may have more than one pair of glasses, with each pair of glasses having support 210 mounted thereon. Accordingly, memory 520 may store information (e.g., personal settings) associated with each pair of glasses. For example, when a user wears his sunglasses may have different preferences than when the user wears reading glasses.

As shown in FIG. 5A, processing unit 140 includes mobile power source 510. Mobile power source 510 may be configured to power processing unit 140 and/or sensory unit 120. The term "mobile power source" includes any device capable of providing electrical power, which can be easily carried by a hand (e.g., the total weight of mobile power source 510 may be less than a pound). Thus, the mobility of the power source enables user 100 to use apparatus 110 in a variety of situations. For example, mobile power source 510 may include one or more batteries (e.g., nickel-cadmium batteries, nickel-metal hydride batteries, and lithium-ion batteries) or any other type of electrical power supply. In some embodiments, mobile power source 510 may be rechargeable and contained within a casing that holds processing unit 140. In other embodiments, mobile power source 510 may include one or more energy harvesting devices for converting ambient energy into electrical energy (e.g., portable solar power units, human vibration units, etc.).

Apparatus 110 may operate in a low-power-consumption mode and in a processing-power-consumption mode. For example, mobile power source 510 can produce five hours of processing-power-consumption mode and fifteen hours of low-power-consumption mode. Accordingly, different power consumption modes may allow mobile power source 510 to produce sufficient power for powering processing unit 140 for various time periods (e.g., more than two hours, more than four hours, more than ten hours, etc.).

Mobile power source 510 may power one or more wireless transceivers (e.g., wireless transceiver 530 in FIG. 5A). The term "wireless transceiver" refers to any device configured to exchange transmissions over an air interface by use of radio frequency, infrared frequency, magnetic field, or electric field. Wireless transceiver 530 may use any known standard to transmit and/or receive data (e.g., Wi-Fi, Bluetooth®, Bluetooth Smart, 802.15.4, or ZigBee). In some embodiments, wireless transceiver 530 may transmit data (e.g., raw image data or audio data) from image sensor 350 to processing unit 140, or wireless transceiver 530 may transmit data from processing unit 140 to feedback-outputting unit 340.

In another embodiment, wireless transceiver 530 may communicate with a different device (e.g., a hearing aid, the user's smartphone, or any wirelessly controlled device) in the environment of user 100. For example, wireless transceiver 530 may communicate with an elevator using a Bluetooth® controller. In such an arrangement, apparatus 110 may recognize that user 100 is approaching an elevator and call the elevator, thereby minimizing wait time. In another example, wireless transceiver 530 may communicate with a smart TV. In such an arrangement, apparatus 110 may recognize that user 100 is watching television and identify specific hand movements as commands for the smart TV (e.g., switching channels). In yet another example, wireless transceiver 530 may communicate with a virtual cane. A virtual cane is any device that uses a laser beam or ultrasound waves to determine the distance from user 100 to an object.

Figure 5B:
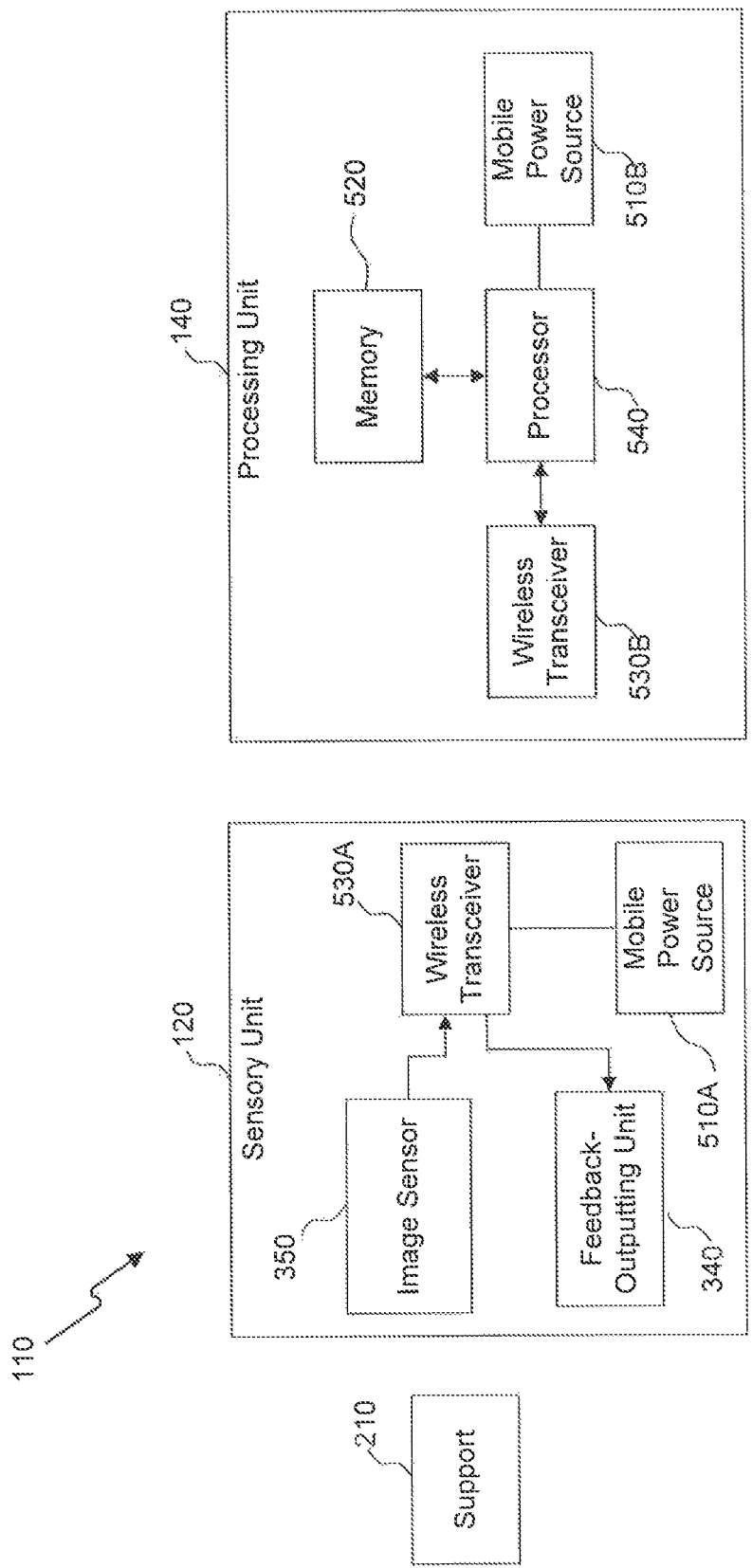
FIG. 5B is a block diagram illustrating an example of the components of an apparatus for aiding persons who have low vision according to a second embodiment.

FIG. 5B is a block diagram illustrating the components of apparatus 110 according to a second embodiment. In FIG. 5B, similar to the arrangement shown in FIG. 5A, support 210 is used to couple sensory unit 120 to a pair of glasses. However, in the embodiment shown in FIG. 5B, sensory unit 120 and processing unit 140 communicate wirelessly. For example, wireless transceiver 530A can transmit image data to processing unit 140 and receive information to be outputted via feedback-outputting unit 340.

In this embodiment, sensory unit 120 includes feedback-outputting unit 340, mobile power source 510A, wireless transceiver 530A, and image sensor 350. Mobile power source 510A is contained within sensory unit 120. As further shown in FIG. 5B, processing unit 140 includes wireless transceiver 530B, processor 540, mobile power source 510B, and memory 520.

Figure 5C:
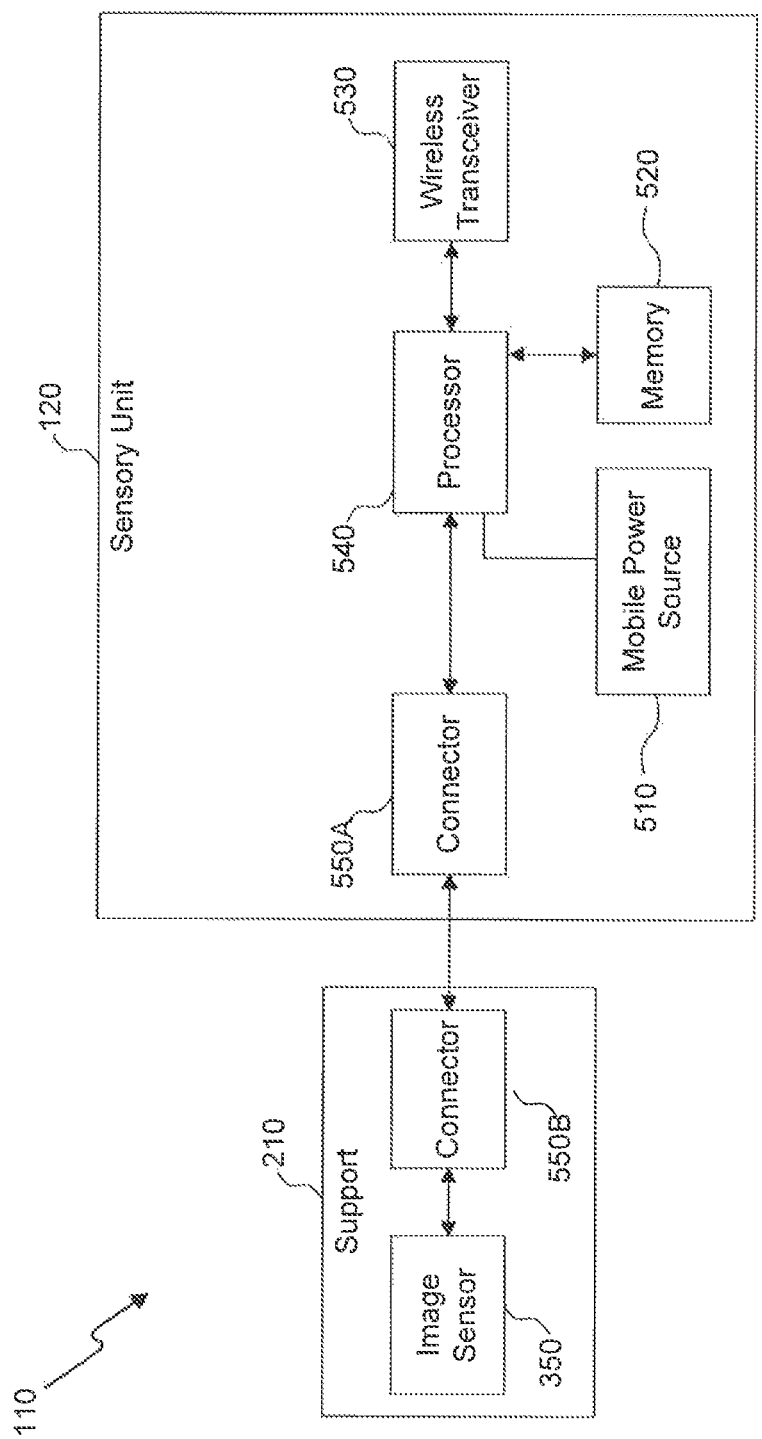
FIG. 5C is a block diagram illustrating an example of the components of an apparatus for aiding persons who have low vision according to a third embodiment.

FIG. 5C is a block diagram illustrating the components of apparatus 110 according to a third embodiment. In particular, FIG. 5C depicts an embodiment in which support 210 includes image sensor 350 and connector 550B. In this embodiment, sensory unit 120 provides functionality for processing data and, therefore, a separate processing unit is not needed in such a configuration.

As shown in FIG. 5C, sensory unit 120 includes processor 540, connector 550A, mobile power source 510, memory 520, and wireless transceiver 530. In this embodiment, apparatus 110 does not include a feedback-outputting unit. Accordingly, wireless transceiver 530 may communicate directly with a hearing aid (e.g., a Bluetooth® hearing aid). In addition, in this embodiment, image sensor 350 is included in support 210. Accordingly, when support 210 is initially mounted on glasses 105, image sensor 350 may acquire a set aiming direction. For example, a camera associated with image sensor 350 may be installed within support 210 in a predetermined angle in a position facing slightly downwards (e.g., 7-12 degrees from the horizon). Furthermore, connector 550A and connector 550B may allow data and power to be transmitted between support 210 and sensory unit 120.

Figure 5D:
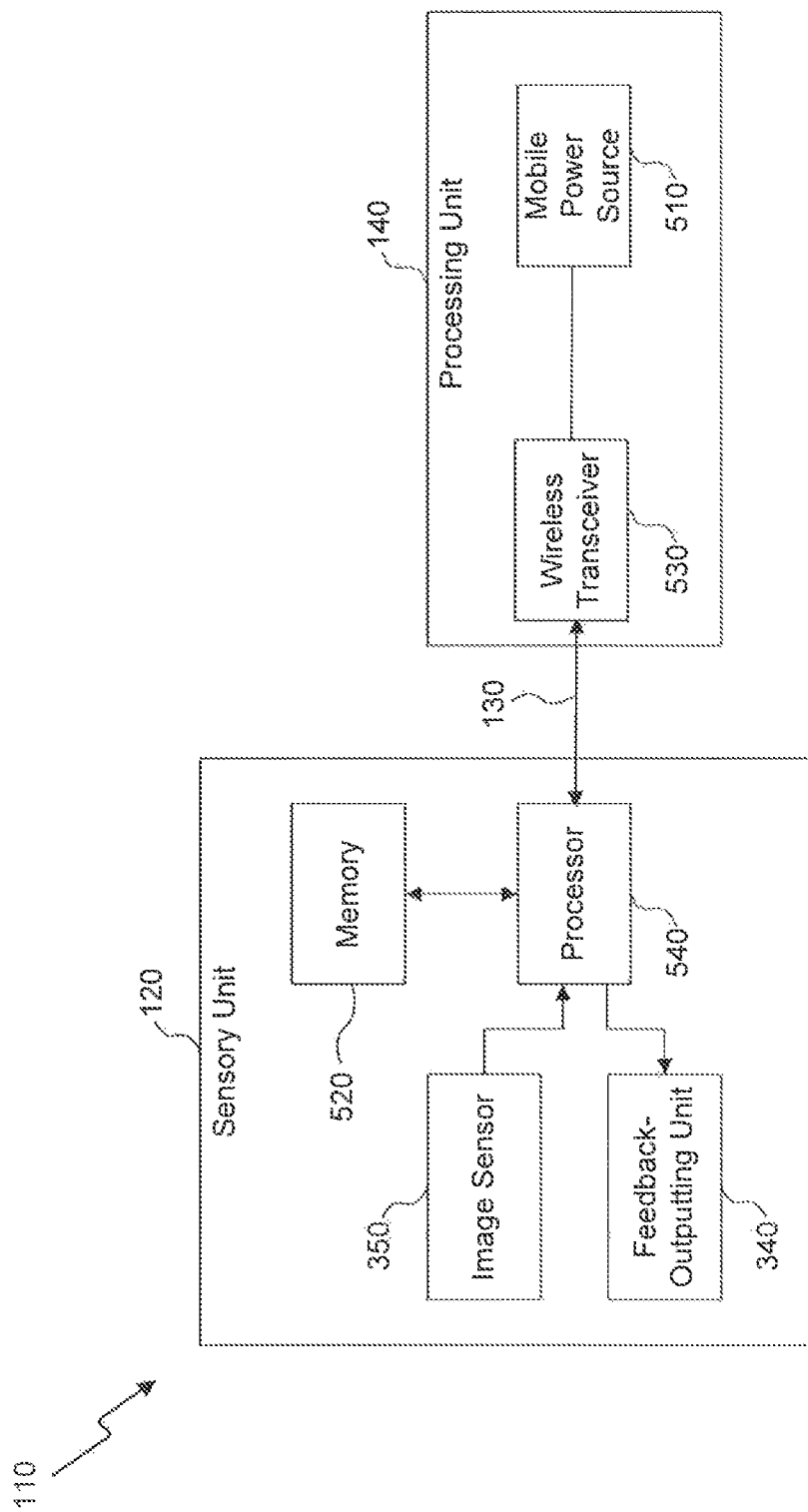
FIG. 5D is a block diagram illustrating an example of the components of an apparatus for aiding persons who have low vision according to a fourth embodiment.

FIG. 5D is a block diagram illustrating the components of apparatus 110 according to a fourth embodiment. In FIG. 5D, sensory unit 120 couples directly to a pair of glasses without the need of a support. In this embodiment, sensory unit 120 includes image sensor 350, feedback-outputting unit 340, processor 540, and memory 520. As shown in FIG. 5D, sensory unit 120 is connected via a wire 130 to processing unit 140. Additionally, in this embodiment, processing unit 140 includes mobile power source 510 and wireless transceiver 530.

As will be appreciated by a person skilled in the art having the benefit of this disclosure, numerous variations and/or modifications may be made to the disclosed embodiments. Not all components are essential for the operation of apparatus 110. Any component may be located in any appropriate part of apparatus 110 and the components may be rearranged into a variety of configurations while providing the functionality of the disclosed embodiments. Therefore, the foregoing configurations are examples and, regardless of the configurations discussed above, apparatus 110 can assist persons who have low vision with their everyday activities in numerous ways.

One way apparatus 110 can assist persons who have low vision is by identifying relevant objects in an environment. For example, in some embodiments, processor 540 may execute one or more computer algorithms and/or signal-processing techniques to find objects relevant to user 100 in image data captured by sensory unit 120. The term "object" refers to any physical object, person, text, or surroundings in an environment.

In one embodiment, apparatus 110 can perform a hierarchical object identification process. In a hierarchical object identification process, apparatus 110 can identify objects from different categories (e.g., spatial guidance, warning of risks, objects to be identified, text to be read, scene identification, and text in the wild) of image data. For example, apparatus 110 can perform a first search in the image data to identify objects from a first category, and after initiating the first search, execute a second search in the image data to identify objects from a second category.

In another embodiment, apparatus 110 can provide information associated with one or more of the objects identified in image data. For example, apparatus 110 can provide information such as the name of an individual standing in front of user 100. The information may be retrieved from a dynamic database stored in memory 520. If the database does not contain specific information associated with the object, apparatus 110 may provide user 100 with nonvisual feedback indicating that a search was made, but the requested information was not found in the database. Alternatively, apparatus 110 may use wireless transceiver 530 to search for and retrieve information associated with the object from a remote database (e.g., over a cellular network or Wi-Fi connection to the Internet).

Another way apparatus 110 can assist persons who have low vision is by performing a continuous action that relates to an object in an environment. A continuous action may involve providing continuous feedback regarding the object. For example, apparatus 110 can provide continuous feedback associated with an object identified within a field-of-view of image sensor 350, and suspend the continuous feedback when the object moves outside the field-of-view of image sensor 350. Examples of continuous feedback may include audibly reading text, playing a media file, etc. In addition, in some embodiments, apparatus 110 may provide continuous feedback to user 100 based on information derived from a discrete image or based on information derived from one or more images captured by sensory unit 120 from the environment of user 100.

Another type of continuous action includes monitoring the state of an object in an environment. For example, in one embodiment, apparatus 110 can track an object as long as the object remains substantially within the field-of-view of image sensor 350. Furthermore, before providing user 100 with feedback, apparatus 110 may determine whether the object is likely to change its state. If apparatus 110 determines that the object is unlikely to change its state, apparatus 110 may provide a first feedback to user 100. For example, if user 100 points to a road sign, apparatus 110 may provide a first feedback that comprises a descriptor of the road sign. However, if apparatus 110 determines that the object is likely to change its state, apparatus 110 may provide a second feedback to user 100 after the object has changed its state. For example, if user 100 points at a traffic light, the first feedback may comprise a descriptor of the current state of the traffic light (e.g., the traffic light is red) and the second feedback may comprise a descriptor indicating that the state of traffic light has changed (i.e., the traffic light is now green).

Apparatus 110 may also determine that an object that is expected to change its state is not functioning and provide appropriate feedback. For example, apparatus 110 may provide a descriptor indicating that a traffic light is broken.

Apparatus 110 can also assist persons who have low vision by making intelligent decisions regarding a person's intentions. Apparatus 110 can make these decisions by understanding the context of a situation. Accordingly, disclosed embodiments may retrieve contextual information from captured image data and adjust the operation of apparatus 110 based on at least the contextual information. The term "contextual information" (or "context") refers to any information having a direct or indirect relationship with an object in an environment. In some embodiments, apparatus 110 may retrieve different types of contextual information from captured image data. One type of contextual information is the time and/or the place that an image of the object was captured. Another example of a type of contextual information is the meaning of text written on the object. Other examples of types of contextual information include the identity of an object, the type of the object, the background of the object, the location of the object in the frame, the physical location of the user relative to the object, etc.

In an embodiment, the type of contextual information that is used to adjust the operation of apparatus 110 may vary based on objects identified in the image data and/or the particular user who wears apparatus 110. For example, when apparatus 110 identifies a package of cookies as an object, apparatus 110 may use the location of the package (i.e., at home or at the grocery store) to determine whether or not to read the list of ingredients aloud. Alternatively, when apparatus 110 identifies a signboard identifying arrival times for trains as an object, the location of the sign may not be relevant, but the time that the image was captured may affect the output. For example, if a train is arriving soon, apparatus 110 may read aloud the information regarding the coming train. Accordingly, apparatus 110 may provide different responses depending on contextual information.

Apparatus 110 may use contextual information to determine a processing action to execute or an image resolution of image sensor 350. For example, after identifying the existence of an object, contextual information may be used to determine if the identity of the object should be announced, if text written on the object should be audibly read, if the state of the object should be monitored, or if an image representation of the object should be saved. In some embodiments, apparatus 110 may monitor a plurality of images and obtain contextual information from specific portions of an environment. For example, motionless portions of an environment may provide background information that can be used to identify moving objects in the foreground.

Yet another way apparatus 110 can assist persons who have low vision is by automatically carrying out processing actions after identifying specific objects and/or hand gestures in the field-of-view of image sensor 350. For example, processor 540 may execute several actions after identifying one or more triggers in image data captured by apparatus 110. The term "trigger" includes any information in the image data that may cause apparatus 110 to execute an action. For example, apparatus 110 may detect as a trigger a finger of user 100 pointing to one or more coins. The detection of this gesture may cause apparatus 110 to calculate a sum of the value of the one or more coins. As another example of a trigger, an appearance of an individual wearing a specific uniform (e.g., a policeman, a fireman, a nurse) in the field-of-view of image sensor 350 may cause apparatus 110 to make an audible indication that this particular individual is nearby.

In some embodiments, the trigger identified in the image data may constitute a hand-related trigger. The term "hand-related trigger" refers to a gesture made by, for example, the user's hand, the user's finger, or any pointed object that user 100 can hold (e.g., a cane, a wand, a stick, a rod, etc.).

In other embodiments, the trigger identified in the image data may include an erratic movement of an object caused by user 100. For example, unusual movement of an object can trigger apparatus 110 to take a picture of the object. In addition, each type of trigger may be associated with a different action. For example, when user 100 points to text, apparatus 110 may audibly read the text. As another example, when user 100 erratically moves an object, apparatus 110 may audibly identify the object or store the representation of that object for later identification.

Apparatus 110 may use the same trigger to execute several actions. For example, when user 100 points to text, apparatus 110 may audibly read the text. As another example, when user 100 points to a traffic light, apparatus 110 may monitor the state of the traffic light. As yet another example, when user 100 points to a branded product, apparatus 110 may audibly identify the branded product. Furthermore, in embodiments in which the same trigger is used for executing several actions, apparatus 110 may determine which action to execute based on contextual information retrieved from the image data. In the examples above, wherein the same trigger (pointing to an object) is used, apparatus 110 may use the type of the object (text, a traffic light, a branded product) to determine which action to execute.

To assist user 100 throughout his or her daily activities, apparatus 100 may follow several procedures for saving processing resources and prolonging battery life. For example, apparatus 110 can use several image resolutions to form images. Higher image resolution provides more detailed images, but requires more processing resources. Lower image resolution provides less detailed images, but saves processing resources. Therefore, to prolong battery life, apparatus 110 may have rules for capturing and processing high resolution image under certain circumstances, and rules for capturing and processing low resolution image when possible. For example, apparatus 110 may capture higher resolution images when performing Optical Character Recognition (OCR), and capture low resolution images when searching for a trigger.

One of the common challenges persons with low vision face on a daily basis is reading. Apparatus 110 can assist persons who have low vision by audibly reading text that is present in user 100 environment. Apparatus 110 may capture an image that includes text using sensory unit 120. After capturing the image, to save resources and to process portions of the text that are relevant to user 100, apparatus 110 may initially perform a layout analysis on the text. The term "layout analysis" refers to any process of identifying regions in an image that includes text. For example, layout analysis may detect paragraphs, blocks, zones, logos, titles, captions, footnotes, etc.

In one embodiment, apparatus 110 can select which parts of the image to process, thereby saving processing resources and battery life. For example, apparatus 110 can perform a layout analysis on image data taken at a resolution of one megapixel to identify specific areas of interest within the text. Subsequently, apparatus 110 can instruct image sensor 350 to capture image data at a resolution of five megapixels to recognize the text in the identified areas. In other embodiments, the layout analysis may include initiating at least a partial OCR process on the text.

In another embodiment, apparatus 110 may detect a trigger that identifies a portion of text that is located a distance from a level break in the text. A level break in the text represents any discontinuity of the text (e.g., a beginning of a sentence, a beginning of a paragraph, a beginning of a page, etc.). Detecting this trigger may cause apparatus 110 to read the text aloud from the level break associated with the trigger. For example, user 100 can point to a specific paragraph in a newspaper and apparatus 110 may audibly read the text from the beginning of the paragraph instead of from the beginning of the page.

In addition, apparatus 110 may identify contextual information associated with text and cause the audible presentation of one portion of the text and exclude other portions of the text. For example, when pointing to a food product, apparatus 110 may audibly identify the calorie value of the food product. In other embodiments, contextual information may enable apparatus 110 to construct a specific feedback based on at least data stored in memory 520. For example, the specific feedback may assist user 100 to fill out a form (e.g., by providing user 100 audible instructions and details relevant to a form in the user's field-of-view).

To improve the audible reading capabilities of apparatus 110, processor 540 may use OCR techniques. The term "optical character recognition" includes any method executable by a processor to retrieve machine-editable text from images of text, pictures, graphics, etc. OCR techniques and other document recognition technology typically use a pattern matching process to compare the parts of an image to sample characters on a pixel-by-pixel basis. This process, however, does not work well when encountering new fonts, and when the image is not sharp. Accordingly, apparatus 110 may use an OCR technique that compares a plurality of sets of image regions that are proximate to each other. Apparatus 110 may recognize characters in the image based on statistics relate to the plurality of the sets of image regions. By using the statistics of the plurality of sets of image regions, apparatus 110 can recognize small font characters defined by more than four pixels e.g., six or more pixels. In addition, apparatus 110 may use several images from different perspectives to recognize text on a curved surface. In another embodiment, apparatus 110 can identify in image data an existence of printed information associated with a system command stored in a database and execute the system command thereafter. Examples of a system command include: "enter training mode," "enter airplane mode," "backup content," "update operating system," etc.

The disclosed OCR techniques may be implemented on various devices and systems and are not limited to use with apparatus 110. For example, the disclosed OCR techniques provide accelerated machine reading of text. In one embodiment, a system is provided for audibly presenting a first part of a text from an image, while recognizing a subsequent part of the text. Accordingly, the subsequent part may be presented immediately upon completion of the presentation of the first part, resulting in a continuous audible presentation of standard text in less than two seconds after initiating OCR.

As is evident from the foregoing, apparatus 110 may provide a wide range of functionality. More specifically, one embodiment consistent with the present disclosure provides a method for providing user 100, who may be visually impaired, with information about one or more objects or situations detected within the field of view of apparatus 110. Apparatus 110 may be configured to monitor real-time image data to determine relative motion between portions of scenes captured within the image data. If one portion of the scene moves less than at least one other portion of the scene, apparatus 110 may be configured to obtain contextual information from that portion of the scene. In some embodiments, apparatus 110 may further provide feedback to the user based on at least part of the contextual information. In other embodiments, apparatus 110 may further adjust one or more parameters associated with image sensor 350 or an associated camera based on at least part of the contextual information.

Figure 6:
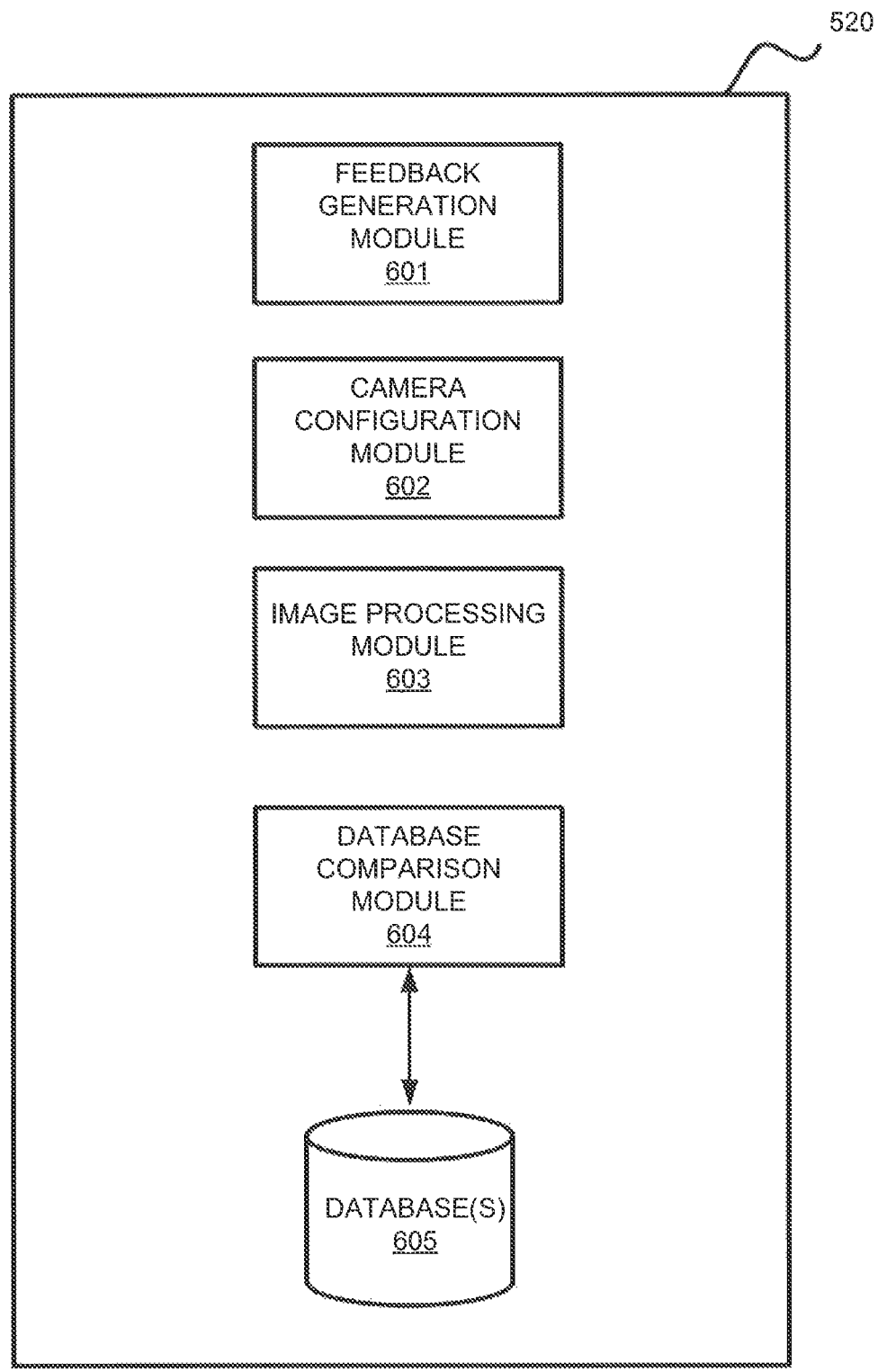
FIG. 6 is a block diagram illustrating an example of a memory contained within an apparatus for aiding persons who have low vision.

FIG. 6 is a block diagram illustrating memory 520 associated with apparatus 110 according to one embodiment. In the example shown in FIG. 6, memory 520 comprises a feedback generation module 601, a camera configuration module 602, an image processing module 603, a database comparison module 604, and one or more databases 605.

Feedback generation module 601 may provide functionality for apparatus 110 to generate and transmit information to user 100 in response to a query. Processor 540 may execute feedback generation module 601 to generate and process feedback in a given context, then transmit the generated feedback to feedback-outputting unit 340 for output to user 100. In one embodiment, processor 540 and feedback-outputting unit 340 may be operatively connected via wire 130. In other embodiments, processor 540 and feedback-outputting unit 340 may be operatively connected via wireless transceiver(s) 530. As discussed above, in some embodiments, feedback generation module 601 may generate audible feedback to user 100. In other embodiments, the feedback may be tactile in nature, such as a vibration.

Camera configuration module 602 may provide functionality for apparatus 110 to capture real-time image data via image sensor 350. Processor 540 may execute camera configuration module 602 to acquire the images, and may additionally use camera configuration module 602 to adjust one or more parameters associated with image sensor 350 and an associated camera. In one embodiment, processor 540 and image sensor 350 may be operatively connected via wire 130. In other embodiments, processor 540 and image sensor 350 may be operatively connected via wireless transceiver(s) 530.

Image processing module 603 may provide functionality for apparatus 110 to analyze sets of real-time image data captured by image sensor 350. Processor 540 may execute image processing module 603, for example, to determine the positions of objects in one or more sets of image data over time, and determine the relative motion of those objects. As discussed above, image processing module 603 may be configured to execute software instructions to perform actions to assist user 100, such as performing optical character recognition on text that is detected within the captured sets of real-time image data.

Database comparison module 604 may provide functionality for apparatus 110 to compare objects detected in the user environment to objects and/or categories of said objects in a database, such as database(s) 605, to be described in detail below. In some embodiments, database comparison module 604 may derive information from real time image data received from image sensor 350. In other embodiments, other software elements or processors may derive the information and provide it to database comparison module 604. Processor 540 may execute database comparison module 604 to access one or more of the described databases, and compare the information derived from the received real time image data with information in the databases. If the derived information corresponds to information found in one or more of the databases, database comparison module 604 may provide an indication to feedback generation module 601 to that effect as discussed in further detail below in association with FIGS. 11-12.

Database(s) 605 may comprise one or more databases that store information and are accessed and/or managed through memory 520. By way of example, databases 605 may include document management systems, Microsoft™ SQL databases, SharePoint™ databases, Oracle™ databases, Sybase™ databases, or other relational databases or non-relational databases, such as Hadoop sequence files, HBase, or Cassandra. The databases or other files may include, for example, data and information related to the source and destination of a network request, the data contained in the request, etc. Systems and methods of disclosed embodiments, however, are not limited to separate databases. Databases 605 may contain software code or macros that facilitate rapid searching and comparison by database comparison module 604.

Feedback generation module 601, camera configuration module 602, image processing module 603, and database comparison module 604 may be implemented in software, hardware, firmware, a mix of any of those, or the like. For example, if the modules are implemented in software, they may be stored in memory 520, as shown in FIG. 6. Other components of processing unit 140 and/or sensory unit 120 may be configured to perform processes to implement and facilitate operations of the modules. Thus, feedback generation module 601, camera configuration module 602, image processing module 603, and database comparison module 604 may include software, hardware, or firmware instructions (or a combination thereof) executable by one or more processors (e.g., processor 540), alone or in various combinations with each other. For example, the modules may be configured to interact with each other and/or other modules of apparatus 110 to perform functions consistent with disclosed embodiments. In some embodiments, any of the disclosed modules (e.g., feedback generation module 601, camera configuration module 602, image processing module 603, and database comparison module 604) may each include dedicated sensors (e.g., IR, image sensors, etc.) and/or dedicated application processing devices to perform the functionality associated with each module.

As used herein, real-time image data may refer to image data captured in real-time or near real-time. For example, image processing module 601 may monitor the field-of-view of apparatus 110 to detect inputs while database comparison module 604 may compare captured image data to stored images. Accordingly, image processing module 601 and while database comparison module 604 may operate in parallel to process captured image data. That is, apparatus 110 may capture and analyze image data in parallel, or may institute a queue-like implementation whereby image data is captured and then analyzed in a continuous fashion (i.e., a first image is captured and analyzed while a subsequent image is captured and then subsequently analyzed).

Figure 7:
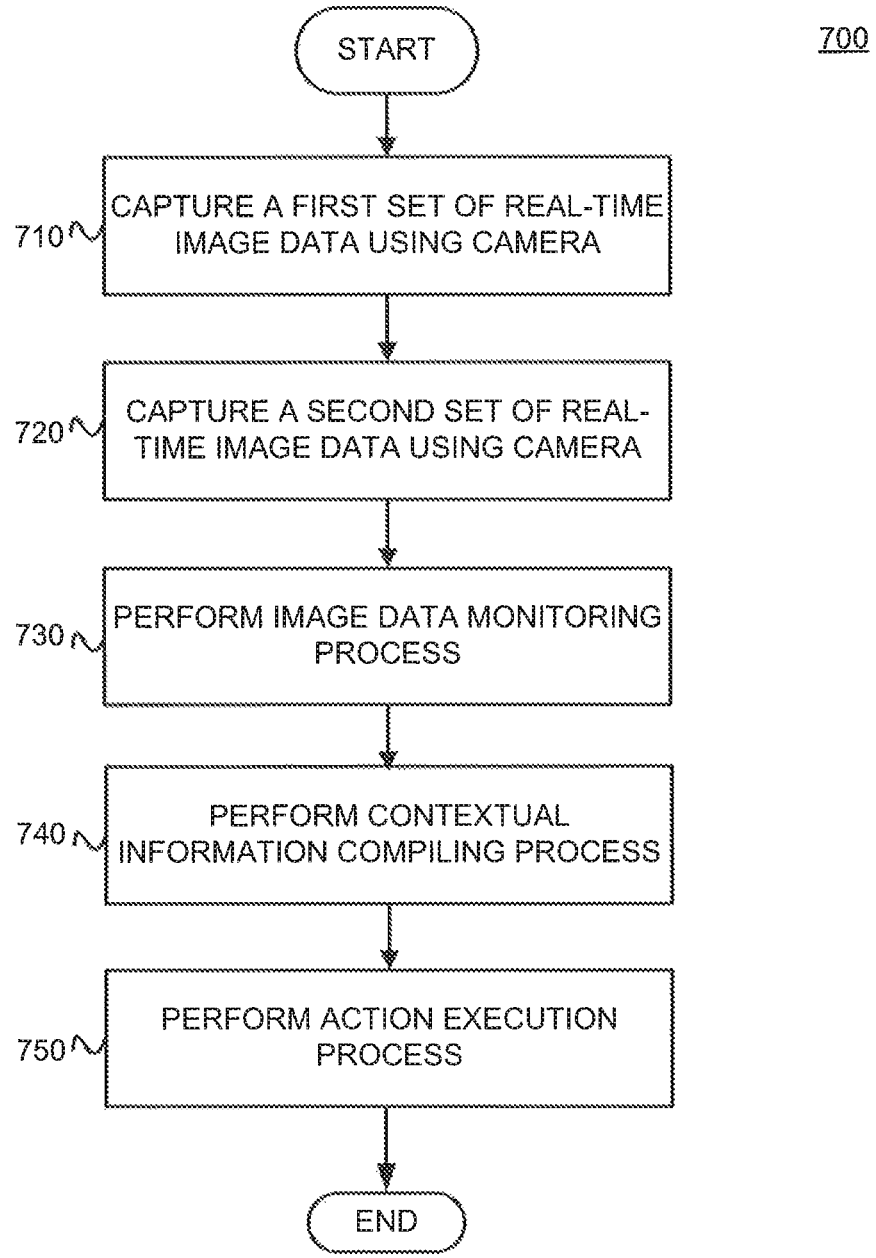
FIG. 7 is an example of a process for providing feedback to a person who has low vision, consistent with disclosed embodiments.

FIG. 7 illustrates an example of a process 700 for providing feedback to a person who has low vision consistent with certain disclosed embodiments. Process 700, as well as any or all of the individual steps therein, may be performed by various aspects of device 110, such as sensory unit 120, processing unit 140, support 210, or any subcomponents therein. For exemplary purposes, FIG. 7 is described as being performed by processor 540, executing software instructions stored within memory 520.

Processor 540 may execute software instructions via camera configuration module 602 that enable apparatus 110 to capture a first set of real-time image data using a camera associated with an image sensor, such as image sensor 350 (Step 710). In some embodiments, processor 540 may receive the captured first set of image data directly from image sensor 350. In other embodiments, processor 540 may receive the captured first set of image data from an intermediate component associated with sensory unit 120. The intermediate unit may, for example, perform image processing operations on the real-time image data before transmitting it to processor 540, as will be discussed in further detail below. In some embodiments, the captured first set of real-time image data may be received as a single streaming video file. In other embodiments, the real-time image data may be received as a series of still images. When the captured image data is received, processor 540 may store the data in memory 520 or database(s) 605.

Processor 540 may execute software instructions via camera configuration module 602 that enable apparatus 110 to capture a second set of real-time image data using a camera associated with an image sensor, such as image sensor 350 (Step 720). The second set of real-time image data may be captured, processed, and received in substantially the same manner as the first set of image data described above. In some embodiments, the captured first set of real-time image data may be received as a single streaming video file. In other embodiments, the real-time image data may be received as a series of still images. When the captured image data is received, processor 540 may store the data in memory 520 or database(s) 605.

In Step 730 of process 700, processor 540, via image processing module 603, may perform an image data monitoring process, such as is described below in connection with FIG. 9. In brief, according to some embodiments, image processing module 603 may load the first and second captured sets of real-time image data. Image processing module 603 may determine positions of one or more objects in the first set of captured real-time image data, and may also do so for the second set of data. Image processing module 603 may determine which of the detected objects are in the foreground of the images within the image data sets, and which of the detected objects are in the background. Image processing module 603 may then determine the relative motion, if any, of the detected objects across the first and second sets of captured image data.

Processor 540 may perform a contextual information compiling process, such as is described below in connection with FIG. 10 (Step 740). In brief, according to some embodiments, processor 540, via image processing module 603, may determine one or more objects across the first and second sets of captured real-time image data that are relatively stationary based on image data monitoring. Processor 540 may also determine one or more moving objects across the two sets of data based on the monitoring. Additionally, processor 540 may determine one or more "lingering" objects of interest across the two sets of data based on the monitoring. Based on the identified images, image processing module 603 may select objects requiring compilation of contextual information. Processor 540 may then compile contextual information on the selected objects.

Processor 540 may perform an action execution process, such as is described below in connection with FIG. 11 (Step 750). In brief, according to some embodiments, processor 540 may select one or more system processing schemes based on compiled contextual information, Based on the selected system processing scheme, processor 540, in conjunction with database comparison module 604, may determine one or more context-based actions associated with the processing scheme. Processor 540 may select one or more of the determined context-based actions, and then execute the selected action(s). Finally, processor 540 may perform a feedback generation process.

Figure 8B:
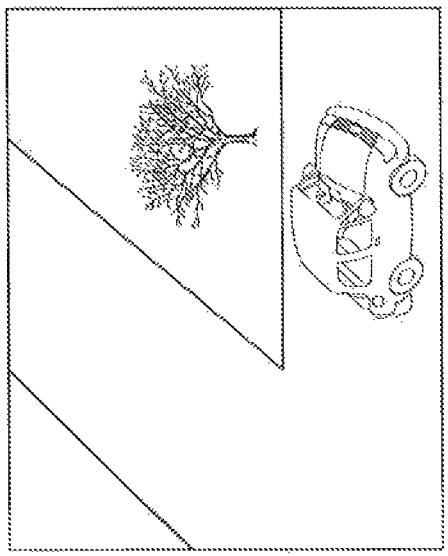
FIGS. 8A and 8B are example illustrations of an object moving through the field of view of an apparatus while the background remains stationary, consistent with disclosed embodiments.
Figure 8D:
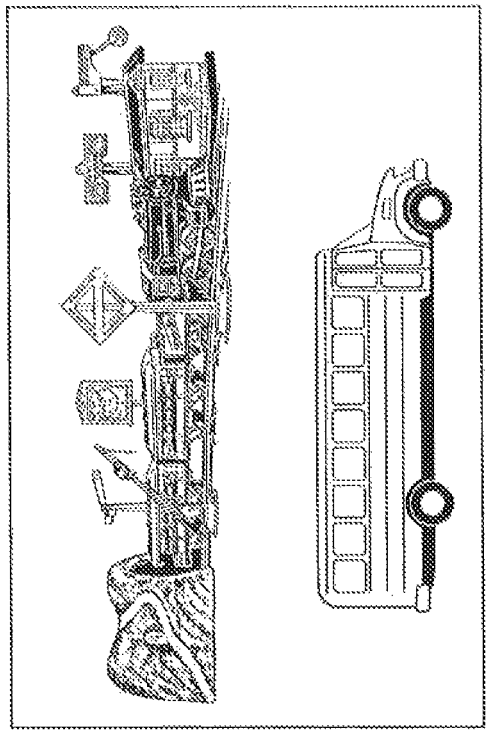
FIGS. 8C and 8D are example illustrations of an object moving through the field of view of an apparatus and being tracked by the head of a user, consistent with disclosed embodiments.
Figure 8A:
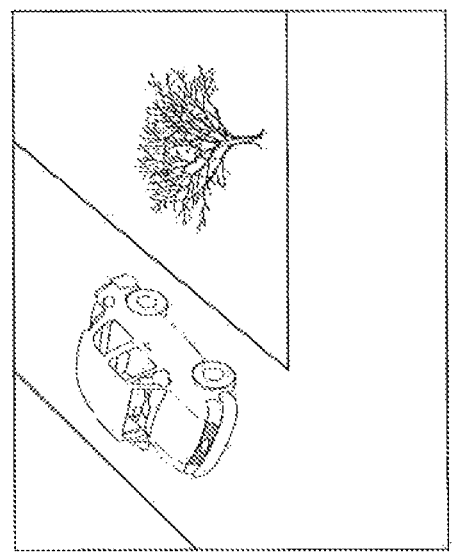

FIGS. 8A-8G illustrate examples of fields of view of apparatus 110, consistent with certain disclosed embodiments. FIGS. 8A-8B illustrate an example field of view of apparatus 110 in which an object is seen to move in the foreground of the field of view while the background remains stationary. In the example of FIG. 8A, a car can be seen approaching an intersection. In FIG. 8B, the car has turned onto the cross street of the intersection. In these embodiments, processor 540 may be configured to obtain contextual information relating to either the moving object (the car) or the stationary background. Apparatus 110 may then perform one or more context-based actions relating to the recognized scene elements.

Figure 8C:
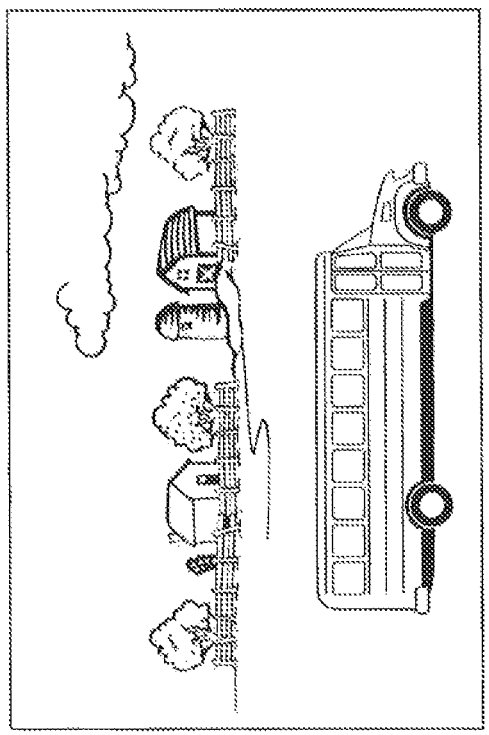

FIGS. 8C-8D illustrate an example field of view of apparatus 110 in which user 100 tracks an object as it moves. Therefore, the tracked object appears to be stationary while the background moves. In the example of FIG. 8C, a bus can be seen passing one background scene. In FIG. 8D, the bus remains in the center of the field of view of apparatus 110 as user 100 tracks its motion with their head, but the background scene behind it has changed. In these embodiments, processor 540 may be configured to obtain contextual information relating to either the object being tracked (e.g., the bus) or the various background fields. Apparatus 110 may then perform one or more context-based actions relating to the recognized scene elements.

Figure 8F:
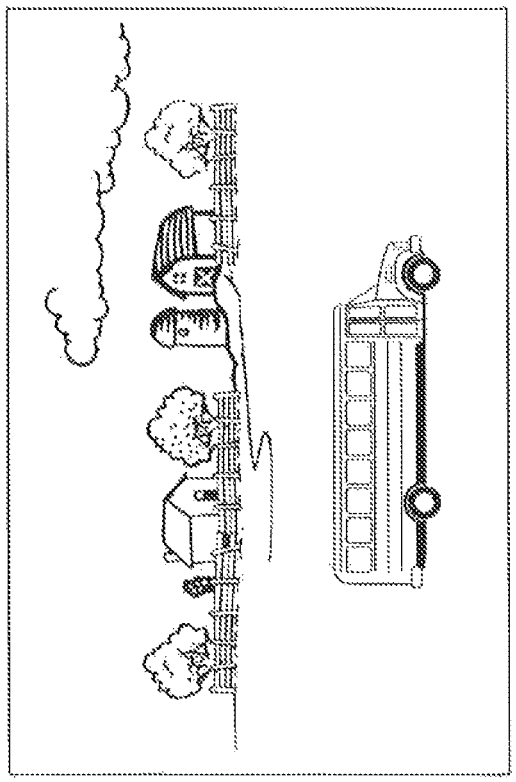
FIGS. 8E, 8F, and 8G are example illustrations of an object lingering in the field of view of an apparatus, consistent with disclosed embodiments.
Figure 8G:
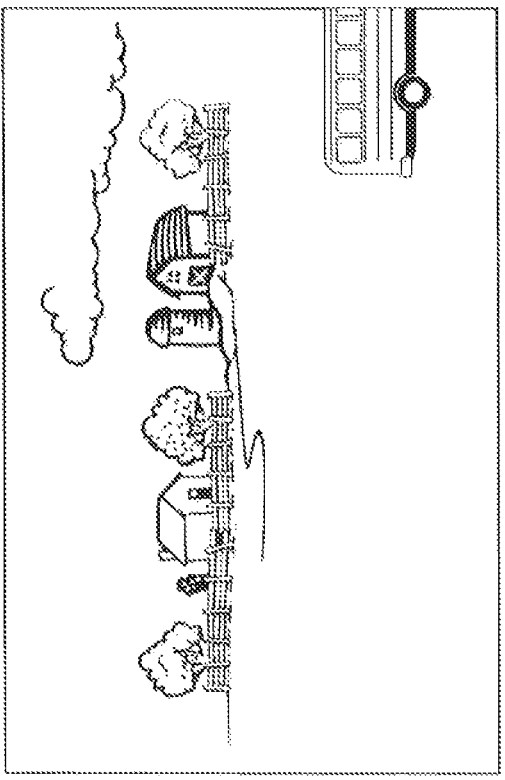
Figure 8E:
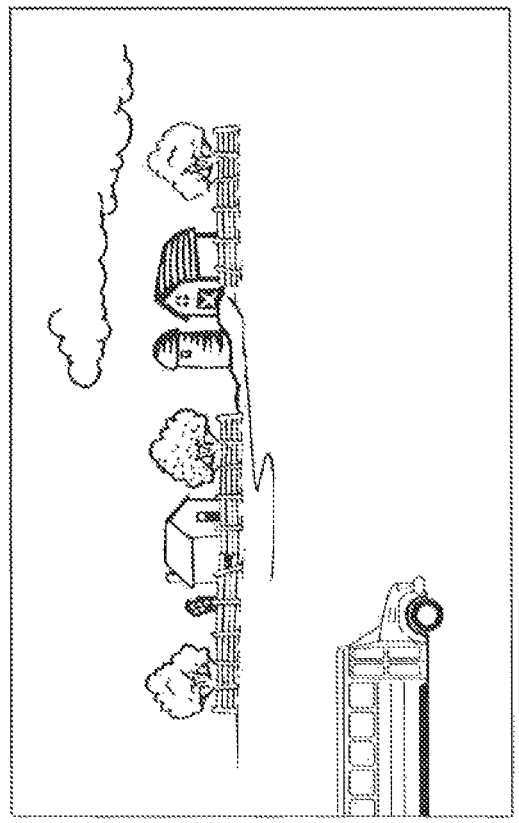

FIGS. 8E, 8F, and 8G illustrate an example field of view of apparatus 110 in which an object enters the field of view, lingers temporarily, then leaves. Therefore, the lingering object moves, then stops, then moves again, while the background remains stationary. In the example of FIG. 8E, a bus can be seen entering the left side of the field of view. In FIG. 8F, the bus is lingering temporarily, and remains in the center of the field of view of apparatus. In FIG. 8G, the bus is moving again, and leaves the field of view to the right. In these embodiments, processor 540 may be configured to obtain contextual information relating to either the lingering object (the bus) or the background. Apparatus 110 may then perform one or more context-based actions relating to the recognized scene elements.

Figure 9:
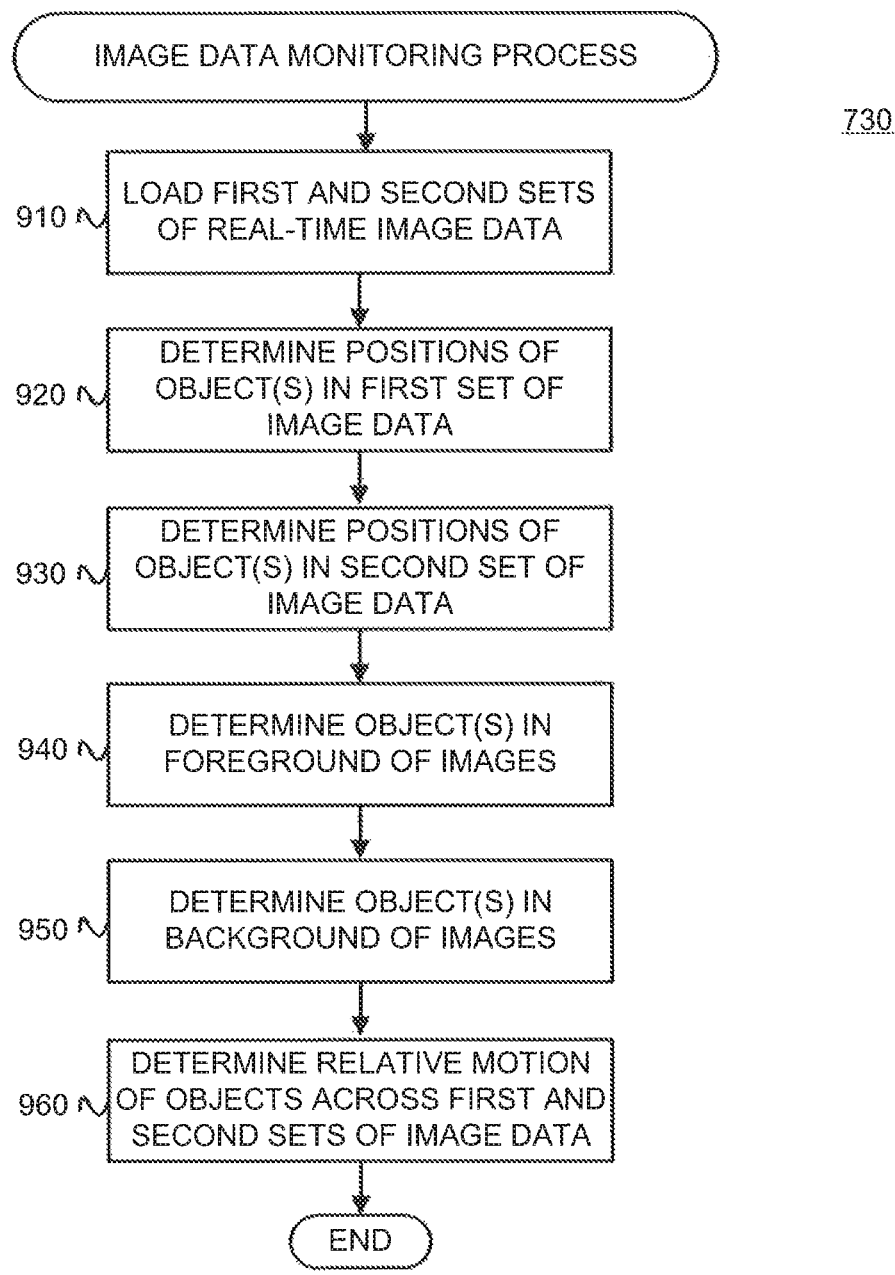
FIG. 9 is an example of an image data monitoring process, consistent with disclosed embodiments.

FIG. 9 illustrates an example image data monitoring process such as that described above in association with Step 730 of process 700, consistent with certain disclosed embodiments. Process 730, as well as any or all of the individual steps therein, may be performed by various aspects of device 110, such as sensory unit 120, processing unit 140, support 210, or any subcomponents therein. For exemplary purposes, FIG. 9 is described as being performed by processor 540, executing software instructions stored within memory 520.

Processor 540, via image processing module 603, may load first and second sets of captured real-time image data (Step 910). Image processing module 603 may determine positions of one or more objects in the first set of captured image data (Step 920). In some embodiments, image processing module 603 may determine the positions of particular objects within the first set of captured image data. In other embodiments, image processing module 603 may instead divide the frames of image data into portions, for example, halves, quadrants, etc. Image processing module 603 may determine the positions of objects or the location of portions by a coordinate system or similar system of referential location. In other embodiments, image processing module 603 may determine the positions of objects or location of portions by relative distance from one or more edges of the field of view of apparatus 110; for example, image processing module 603 may register the position of an object or the location of a portion by the number of pixels the object is away from the top and left sides of the field of view. Positions of objects may be determined by their edges, their centers/centroids, or by any method known to those skilled in the art of image processing. Image processing module 603 may repeat Step 920 for the second captured set of image data, and for any subsequent sets of captured image data (Step 930).

Image processing module 603 may determine one or more objects in the foreground of the images captured in one or both of the first and second sets of captured real-time image data (Step 940). In some embodiments, image processing module 603 may determine that an object is in the foreground based on the focus of the image. In these embodiments, processor 540 may additionally call camera configuration module 602 in order to determine the center of focus of the image, the focal length of the lens of image sensor 350, or any other parameter of image sensor 350 and any associated camera(s) that may assist in determining the depth of field of the image data. In some embodiments, image processing module 603 may determine that an object is in the foreground of an image based on its proximity to a known, recognized object that is detected within the image data. For example, if information about a bus stop has been previously stored within database(s) 605, processor 540 may detect that the bus stop appears in the field of view of apparatus 110, by way of image processing module 603 and database comparison module 604. If a second, novel object of interest such as a bus is determined to be between user 100 and the known bus stop, image processing module 603 may determine that the bus is in the "foreground" of the image. Image processing module 603 may determine that objects are in the "background" of the image by similar methods (Step 950). It is to be understood that "foreground" and "background" as used in this specification are relative terms, and that the terms are not tied to any specific dimensional meaning or distance measurement.

Image processing module 603 may determine relative motion of one or more of the determined objects across the first and second captured sets of image data (Step 960). In some embodiments, camera configuration module 602 and/or image processing module 603 may determine that the position of an object changed from the time that the first set of image data was captured to the time that the second set of images was captured. As an example, in the illustration described above with respect to FIGS. 8A-8B, the car in FIG. 8A made a left turn at the intersection shown in FIG. 8A, and is therefore in a different position in FIG. 8B. In that example, FIG. 8A may comprise a first set of captured image data, and FIG. 8B may comprise a second set of such data. Image processing module 603 may determine that the object in question changed position by detecting that an edge of the object or a determined center/centroid of the object is not at the same position in the second set of captured image data as it was in the first set of such data. In embodiments where image processing module 603 is configured to use a coordinate system for position determination, image processing module 603 may determine that the edge or center/centroid of the object of interest is at a different coordinate position in the second set of captured image data versus the first set of such data. Alternatively, in embodiments where image processing module 603 divides the field of view of apparatus 110 into portions, image processing module 603 may gauge relative motion of objects within the individual portions, or may focus on the field of view as a whole to determine whether relative motion occurs between a first portion of a scene and other portions of the scene captured in the plurality of images comprising the first and second sets of image data.

Figure 10:
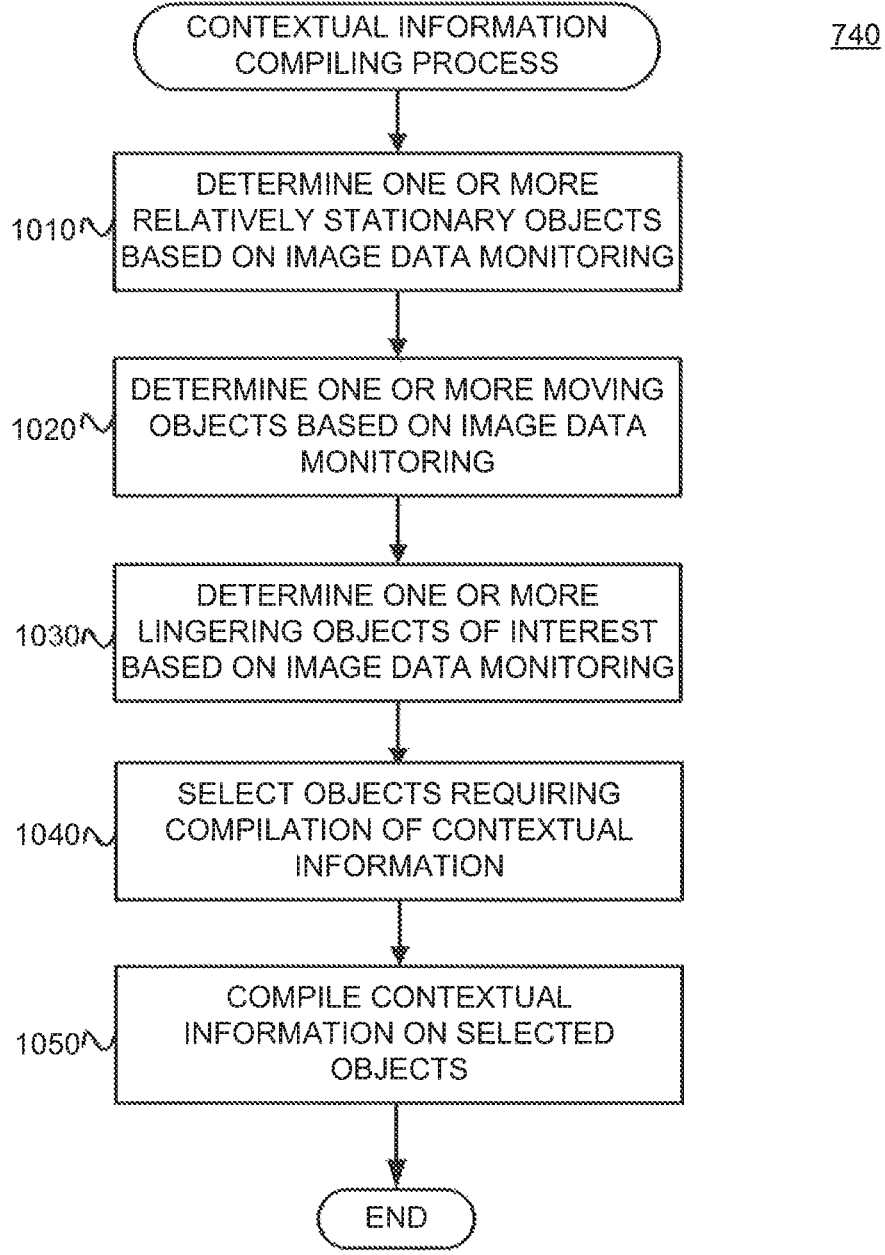
FIG. 10 is an example of a contextual information compiling process, consistent with disclosed embodiments.

FIG. 10 illustrates an example contextual information compiling process such as that described above in association with Step 740 of process 700 consistent with certain disclosed embodiments. Process 740, as well as any or all of the individual steps therein, may be performed by various aspects of device 110, such as sensory unit 120, processing unit 140, support 210, or any subcomponents therein. For exemplary purposes, FIG. 10 is described as being performed by processor 540, executing software instructions stored within memory 520.

Based on the relative motion determinations described above in association with FIG. 9 and example image data monitoring process 730, processor 540, via image processing module 603, may determine and evaluate a motion status of various objects identified within the field of view of apparatus 110. For example, image processing module 603 may determine that one or more objects were stationary in the scene based on the image data monitoring (Step 1010). Image processing module 603 may determine that an object was relatively stationary based on a determination that there was little to no relative motion of the object between a first and second set of captured image data. In some embodiments, a stationary object may be determined to be an object in the background of the image, as discussed above. These stationary objects may be permanent elements of a scene. For example, in the illustration of FIGS. 8A-8B described above, stationary objects might include the two streets comprising the intersection. In other embodiments, an object may appear relatively stationary even though in reality it is moving. This may occur because user 100's head is tracking the object as it moves. For example, in the illustration of FIGS. 8C-8D described above, the bus appears relatively stationary as the background changes behind it because user 100 is tracking the bus.

Similarly, image processing module 603 may determine one or more moving objects in the scene based on the image data monitoring (Step 1020). Image processing module 603 may determine that an object was moving based on a determination that there was detectable relative motion of the object between a first and second set of captured image data. For example, in the illustration of FIGS. 8A-8B described above, the car would be determined to be a moving object because in FIG. 8A the car is traveling down one cross street comprising an intersection, and in FIG. 8B the car has turned and is traveling down the other cross street. In other embodiments, an object may appear to be moving even though in reality it is relatively stationary. This may occur because user 100's head is tracking another moving object as it moves. For example, in the illustration of FIGS. 8C-8D described above, the scenery behind the bus appears to be moving because user 100 is tracking the bus.

In another embodiment, image processing module 603 may determine one or more "lingering" objects of interest within the first and second sets of captured image data based on the image data monitoring (Step 1030). Image processing module 603 may determine that an object is lingering based on a determination that there were one or more periods of relative motion of the object between a first and second set of captured image data, and also one or more periods when the object was relatively stationary. For example, in the illustration of FIGS. 8E-8G described above, the bus enters the field of view in FIG. 8E, lingers in FIG. 8F, and then departs in FIG. 8G.

Image processing module 603 may select one or more objects in the first and/or second sets of captured image data that require compilation of information relating to context (Step 1040). In some embodiments, processor 540 and image processing module 603 may determine that contextual information about an object in the background of the image data is needed to identify an item in the foreground of the image data, or vice versa. In some embodiments, processor 540 and image processing module 603 may determine that contextual information about a moving object in the image data is needed to identify a stationary object in the image data, or vice versa. In some embodiments, as discussed above, image processing apparatus may determine that an object identified in the image data is a branded product, and that contextual information is needed about the brand or the particular product. In some embodiments, processor 540 and image processing module 603 may determine that contextual information is needed about a moving object that appears relatively stationary because the head of user 100 wearing apparatus 110 is tracking it. It is to be understood that these are non-limiting examples, and that any particular situation may present a need for apparatus 110 to compile contextual information on a particular object, scene, or other element captured in real-time image data via image sensor 350.

Processor 540, via image processing module 603 and database comparison module 604, may compile contextual information on the selected objects (Step 1050). In some embodiments, apparatus 110 may recognize a familiar context associated with the object based on prior experience, or based, for example, on context information pre-programmed into memory 520 or database(s) 605. In these embodiments, database comparison module 604 may identify known and familiar contexts associated with objects and triggers within database(s) 605. Alternatively, the context determined from the image sensor data may not be recognized or familiar, and processor 540 may prompt user 100 to provide information relating to the context via an audio prompt or via a user interface visible to user 100 within the field of view of apparatus 110. Apparatus 110 may receive the context information in these embodiments from user 100, and then database comparison module 604 may use the received information to search database(s) 605 for relevant entries. Alternatively, as described above, database comparison module 604 may determine that an object also appearing in the image data has a known context, and may use that contextual information to compile the same information for any objects with unknown or unfamiliar contexts. In some embodiments, compiling the contextual information may include comparing a portion of a scene captured in the first or second sets of image data to stored image data. In other embodiments, compiling the contextual information may include performing additional image processing on one or more areas of the images comprising the first or second sets of image data. For example, image processing module 603 may determine that text is present in the image data, and may perform optical character recognition on an area of at least one of the images within the image data sets. These descriptions are intended as non-limiting examples; processor 540 may undertake any operable means of compiling contextual data.

Figure 11:
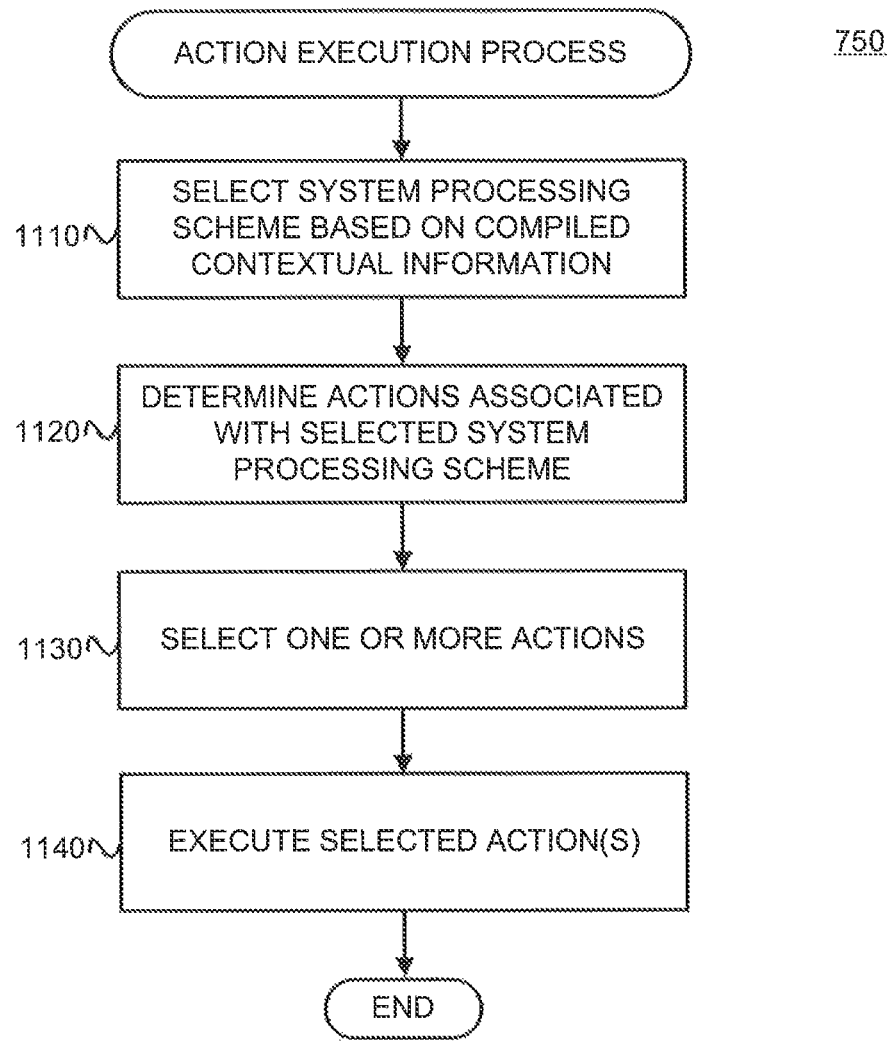
FIG. 11 is an example of an action execution process, consistent with disclosed embodiments.

FIG. 11 illustrates an example action execution process such as that described above in association with Step 750 of process 700 consistent with certain disclosed embodiments. Process 750, as well as any or all of the individual steps therein, may be performed by various aspects of device 110, such as sensory unit 120, processing unit 140, support 210, or any subcomponents therein. For exemplary purposes, FIG. 11 is described as being performed by processor 540, executing software instructions stored within memory 520.

In some embodiments, processor 540 may select a system processing scheme for apparatus 110 based on the compiled contextual information (Step 1110). As discussed above, processor 540 may determine object context in a contextual information compiling process based on real-time image data received from image sensor 350. In other embodiments, processor 540 may determine object context based on real-time audio data received from image sensor 350. In some embodiments, apparatus 110 may recognize a familiar context associated with the object based on prior experience, or based, for example, on context information pre-programmed into memory 520 or database(s) 605. In these embodiments, database comparison module 604 may identify known and familiar processing schemes for processor 540 and apparatus 110 associated with the identified objects, backgrounds, and contextual information within database(s) 605. Alternatively, if the objects, backgrounds, or contexts are not recognized or familiar, processor 540 may prompt user 100 to provide information relating to the context via an audio prompt or via a user interface visible to user 100 within the field of view of apparatus 100. Apparatus 110 may receive the context information in these embodiments from user 100, and then database comparison module 604 may use the received information to search database(s) 605 for relevant entries. For example, in some embodiments, the selected processing scheme may identify an object. In some embodiments, the selected processing scheme may identify an individual. In other embodiments, the processing scheme may audibly read text, or may continuously monitor an object.

Additionally, processor 540 may determine one or more context-based actions associated with the selected system processing scheme (Step 1120). In some embodiments, processor 540 performs such actions in addition to any feedback generated by feedback generation module 601. In other embodiments, the actions are performed instead of the feedback generation.

One skilled in the art may contemplate a multitude of actions that may be associated with a given processing scheme. As discussed above, actions may include, but not be limited to, audibly reading text, sending an electronic message or instant message over the Internet; configuring settings for apparatus 110 or image sensor 350; activating a user interface, which may appear on the lens of the glasses within the vision of user 100 and provide additional interactivity options, announcing an identity of an inanimate object, announcing an identity of an individual, identifying a scene perceived within the field of view, tracking an object, summing money, monitoring a status of a traffic light, saving an individual's name, audibly reading a summary of text, monitoring an object expected to change, identifying a bus number, identifying currency, identifying a credit card, or identifying a pharmaceutical product, such as a pill.

Various actions available for execution by processor 540 may be stored in database entries within database(s) 605 associated with various objects and triggers. In these embodiments, processor 540 may call database comparison module 604 to access and extract possible alternative actions, then transmit the possible actions to processor 540 for execution.

Processor 540 may select one or more of the context-based actions presented for execution (Step 1130). In some embodiments, processor 540 may select a single action for execution based on the context. In other embodiments, processor 540 may select multiple actions. In these embodiments, one or more of the actions may be sequential; for example, an action may only be executed if another particular action is executed beforehand.

Upon selecting one or more of the actions, processor 540 may execute various software instructions to perform the action (Step 1140). For example, in some embodiments, the context-based action may comprise providing feedback to the user based on at least part of the contextual information. In these embodiments, processor 540 may employ feedback generation module 601 and feedback-outputting unit 430 to generate, configure, and output the feedback, as will be discussed in further detail below. In some embodiments, the feedback may comprise audible feedback; in other embodiments, the feedback may be of a tactile nature.

In other embodiments, processor 540 may call camera configuration module 602 to perform a context-based action associated with the configuration of apparatus 110 itself. In these embodiments, image sensor 350 may comprise a camera, and camera configuration module 602 may, based on at least part of the contextual information, adjust at least one parameter associated with the camera. The camera-associated parameter may include at least one of a focus point, an exposure time, an aperture size, light sensitivity, an image resolution, and a frame rate. This list of parameters is intended to be exemplary, and any other parameter or setting associated with cameras may be altered as part of the execution of the context-based action. Adjusting the camera settings in this manner may permit apparatus 110 to adjust to changing circumstances in the environment of user 100, such as availability of light at a particular time of day or in particular weather conditions. Additionally, processor 540 may use camera configuration module 602 to check and verify the operational status of image sensor 350, and if needed, may assist with maintenance of apparatus 110.

In some embodiments, processor 540 may be configured to rapidly adjust the alternative actions available to processor 540 based in changes that may be identified in one or more of a trigger, an identified object, or a context related to the object. In these embodiments, as these elements change, processor 540 may call database comparison module 604 to search database(s) 605 for new alternative actions associated with the newly-changed trigger, object, or context.

As a non-limiting example of process for providing information to a user (such as user 100) who may be visually-impaired, such as that described above in association with FIG. 7, apparatus 110 may determine that user 100 is visually tracking an object, such as the bus illustrated in FIGS. 8C-8D, and needs to identify it. Via camera configuration module 602, processor 540 may execute software instructions enabling apparatus 110 (via image sensor 350) to capture at least two sets of real-time image data across a period of time. Via image processing module 603, processor 540 may monitor the image data, and determine various objects in the background that the bus passes, as well as their relative motion over time. Via database comparison module 604, processor 540 may compile contextual information from the background objects to help determine the identity of the bus. Database comparison module 604 may compare the compiled contextual information to existing information in database(s) 605, and determine the identity of the bus. Finally, processor 540 may execute software instructions to provide feedback to user 100 via feedback generation module 601 and feedback-outputting unit 430 identifying the bus to user 100. This feedback generation process will now be described in further detail.

Figure 12:
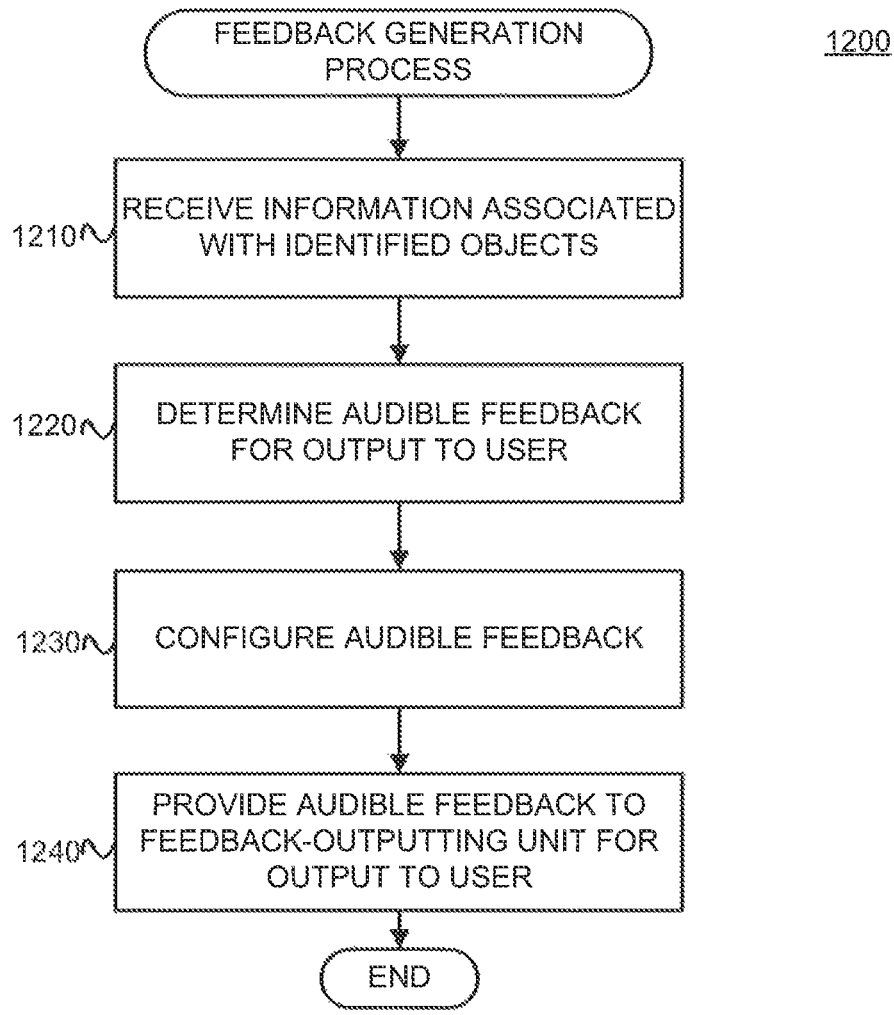
FIG. 12 is an example of a feedback generation process, consistent with disclosed embodiments.

FIG. 12 illustrates an example feedback generation process 1200 consistent with certain disclosed embodiments. Process 1200, as well as any or all of the individual steps therein, may be performed by various aspects of device 110, such as sensory unit 120, processing unit 140, support 210, or any subcomponents therein. For exemplary purposes, FIG. 12 is described as being performed by processor 540, executing software instructions stored within memory 520.

As discussed above, in some embodiments, processor 540 may perform a context-based action (for example, in Step 1140 of action execution process 750 discussed above) after analyzing real-time image data and using changes in relative motion in different portions of the image to determine context. In some embodiments, the context-based action may comprise providing feedback to user 100 via apparatus 110. Process 1200 is an example feedback generation process describing how processor 540 may execute such an action. Processor 540, via feedback generation module 601, may receive information associated with one or more identified objects that have been determined to be present in the environment surrounding user 100 (Step 1210). The received information may further comprise information relating to a result of one or more executed alternative actions, as discussed above. Based on the received information, feedback generation module 601 may determine audible feedback for output to user 100 (Step 1220). In some embodiments, the identified object or executed alternative action may each already be associated with an audible feedback file stored in memory 520 or database(s) 605. In these embodiments, feedback generation module 601 may simply access the existing associated audible feedback file and prepare it for transmission. In other embodiments, there may be multiple audible feedback files associated with the identified object(s) or actions, and feedback generation module may review the determined trigger and/or context information to determine the correct associated audible feedback to output to user 100. In still other embodiments, there may be no existing audible feedback associated with the identified object(s) or actions. In these embodiments, feedback generation module 601 may determine content for audible feedback by prompting user 100 for the feedback, or may infer proper audible feedback, based on context and based on other objects within the category.

Upon determining the proper audible feedback to use, feedback generation module 601 may configure the audible feedback into a readable format, if necessary (Step 1230), then provide the audible feedback to feedback-outputting unit 430 for output to user 100 (Step 1240). Feedback generation module 601 may provide the feedback to feedback-outputting unit 430 via wire 130, or alternatively, via wireless transceiver(s) 530.

The foregoing description has been presented for purposes of illustration. It is not exhaustive and is not limited to the precise forms or embodiments disclosed. Modifications and adaptations will be apparent to those skilled in the art from consideration of the specification and practice of the disclosed embodiments. Additionally, although aspects of the disclosed embodiments are described as being stored in memory, one skilled in the art will appreciate that these aspects can also be stored on other types of computer readable media, such as secondary storage devices, for example, hard disks, floppy disks, or CD ROM, or other forms of RAM or ROM, USB media, DVD, or other optical drive media.

Computer programs based on the written description and disclosed methods are within the skill of an experienced developer. The various programs or program modules can be created using any of the techniques known to one skilled in the art or can be designed in connection with existing software. For example, program sections or program modules can be designed in or by means of .Net Framework, .Net Compact Framework (and related languages, such as Visual Basic, C, etc.), Java, C++, Objective-C, HTML, HTML/AJAX combinations, XML, or HTML with included Java applets. One or more of such software sections or modules can be integrated into a computer system or existing e-mail or browser software.

Moreover, while illustrative embodiments have been described herein, the scope of any and all embodiments having equivalent elements, modifications, omissions, combinations (e.g., of aspects across various embodiments), adaptations and/or alterations as would be appreciated by those skilled in the art based on the present disclosure. The limitations in the claims are to be interpreted broadly based on the language employed in the claims and not limited to examples described in the present specification or during the prosecution of the application. The examples are to be construed as non-exclusive. Furthermore, the steps of the disclosed routines may be modified in any manner, including by reordering steps and/or inserting or deleting steps. It is intended, therefore, that the specification and examples be considered as illustrative only, with a true scope and spirit being indicated by the following claims and theft full scope of equivalents.

What is claimed is:

1. An apparatus for providing feedback to a user, the apparatus comprising:
    an image sensor configured to be positioned for movement with a head of the user as the head moves, and to capture real time images from an environment of the user; and
    at least one processor device for determining contextual information based on the real time images, the processor device being configured to:
    monitor a plurality of images captured by the image sensor to determine whether relative motion occurs between a first portion of a scene captured in the plurality of images and other portions of the scene captured in the plurality of images;
    if the first portion of the scene moves less than at least one other portion of the scene, obtain contextual information from the first portion of the scene; and
    provide the feedback to the user based on at least part of the contextual information.

2. The apparatus of claim 1, wherein the first portion of the scene is associated with an object in a background of the scene, and the at least one other portion of the scene is associated with an object in a foreground of the scene.

3. The apparatus of claim 2, wherein the contextual information associated with the object in the background is used to identify the object in the foreground.

4. The apparatus of claim 2, wherein the at least one processor device is further configured to retrieve contextual information from a stationary object in the background when the object in the foreground is moving.

5. The apparatus of claim 4, wherein the stationary object includes a branded product and the contextual information includes information associated with the branded product.

6. The apparatus of claim 1, wherein the first portion of the scene is associated with an object in a foreground and the at least one other portion of the scene is associated with an object in the background.

7. The apparatus of claim 6, wherein the at least one processor device is further configured to retrieve contextual information from a moving object in a foreground of the scene when the user's head tracks the moving object.

8. The apparatus of claim 7, wherein the moving object includes a public transportation vehicle and the contextual information includes information associated with the public transportation vehicle.

9. The apparatus of claim 1, wherein obtaining contextual information includes performing optical character recognition on an area of at least one of the plurality of images associated with the first portion of the scene.

10. The apparatus of claim 1, wherein obtaining contextual information includes comparing the first portion of the scene with stored image data.

11. The apparatus of claim 1, wherein the contextual information is used for selecting an action to execute from a plurality of context-based actions.

12. The apparatus of claim 1, wherein the image sensor is further configured to capture real time images at a plurality of resolutions, and the contextual information is used for selecting which of the plurality of resolutions to use.

13. The apparatus of claim 1, wherein the at least one processor device is configured to select between a plurality of differing processing schemes based on the contextual information obtained.

14. The apparatus of claim 13, wherein the plurality of differing processing schemes includes a processing scheme to identify an object, a processing scheme to identify an individual, a processing scheme to audibly reading a text, and a processing scheme to continuously monitor an object.

15. A method for providing feedback to a user, the method comprising:
    obtaining from an image sensor a plurality of images, wherein the image sensor is configured to be positioned for movement with a head of the user;

monitoring the plurality of images captured by the image sensor;

determining whether relative motion occurs between a first portion of a scene captured in the plurality of images and other portions of the scene captured in the plurality of images;

if the first portion of the scene moves less than the at least one other portion of the scene, obtaining contextual information from the first portion of the scene; and providing the feedback to the user based on at least part of the contextual information.

16. A software product stored on a non-transitory computer readable medium and comprising data and computer implementable instructions for carrying out the method of claim 15.

17. The method of claim 15, wherein the first portion of the scene is associated with an object in a background of the scene, and the at least one other portion of the scene is associated with an object in a foreground of the scene.

18. The method of claim 15, wherein the contextual information associated with the object in the background is used to identify the object in the foreground.

19. The method of claim 15, the method further comprising retrieving contextual information from a stationary object in the background when the object in the foreground is moving.

20. The method of claim 15, wherein the stationary object includes a branded product and the contextual information includes information associated with the branded product.

21. The method of claim 15, the method further comprising
determining that an object appears to be stationary in the first portion of the scene across the monitored images while the other portions of the scene appear to be moving across the monitored images;
determining, from the monitored images, based on the stationary appearance of the object in the first portion of the scene across the monitored images while the other portions of the scene appear to be moving across the monitored images, that the head of a user is tracking the object included in the first portion of the scene,
wherein the object appears to be stationary across the monitored images while the other portions of the scene appear to be moving across the monitored images; and
obtaining contextual information associated with the object that the head of the user is tracking.

\* \* \* \* \*